US011919919B2

(12) United States Patent
Khanzhin et al.

(10) Patent No.: US 11,919,919 B2
(45) Date of Patent: *Mar. 5, 2024

(54) SYNTHESIS OF OLIGOSACCHARIDES

(71) Applicant: GLYCOM A/S, Hørsholm (DK)

(72) Inventors: Nikolay Khanzhin, Humlebæk (DK);
Markus Jondelius Hederos, Trelleborg (SE)

(73) Assignee: GLYCOM A/S, Hørsholm (DK)

( * ) Notice: Subject to any disclaimer, the term of this patent is extended or adjusted under 35 U.S.C. 154(b) by 254 days.

This patent is subject to a terminal disclaimer.

(21) Appl. No.: 17/646,093

(22) Filed: Dec. 27, 2021

(65) Prior Publication Data

US 2022/0119437 A1    Apr. 21, 2022

Related U.S. Application Data

(63) Continuation of application No. 16/626,245, filed as application No. PCT/IB2018/054753 on Jun. 27, 2018, now Pat. No. 11,214,588.

(30) Foreign Application Priority Data

| Jun. 30, 2017 | (DK) | ................................ | 2017 70522 |
| Jun. 30, 2017 | (DK) | ................................ | 2017 70523 |
| Jun. 30, 2017 | (DK) | ................................ | 2017 70524 |

(51) Int. Cl.

| *C07H 1/06* | (2006.01) |
| *A23L 3/00* | (2006.01) |
| *A23L 33/00* | (2016.01) |
| *B01D 61/02* | (2006.01) |
| *B01D 61/04* | (2006.01) |
| *B01D 61/14* | (2006.01) |
| *B01D 61/58* | (2006.01) |
| *B01D 69/02* | (2006.01) |
| *B01D 69/12* | (2006.01) |
| *B01D 71/56* | (2006.01) |
| *B01D 71/58* | (2006.01) |
| *C07H 3/06* | (2006.01) |
| *C08B 37/00* | (2006.01) |
| *C12P 19/04* | (2006.01) |
| *C12P 19/12* | (2006.01) |
| *C12P 19/18* | (2006.01) |

(52) U.S. Cl.
CPC ............... *C07H 1/06* (2013.01); *A23L 33/40* (2016.08); *B01D 61/027* (2013.01); *B01D 61/04* (2013.01); *B01D 61/146* (2022.08); *B01D 61/58* (2013.01); *B01D 69/02* (2013.01); *B01D 69/12* (2013.01); *B01D 71/56* (2013.01); *B01D 71/58* (2013.01); *C07H 3/06* (2013.01); *C08B 37/0003* (2013.01); *C12P 19/04* (2013.01); *C12P 19/12* (2013.01); *C12P 19/18* (2013.01); *A23L 33/00* (2016.08); *A23V 2002/00* (2013.01); *B01D 61/145* (2013.01); *B01D 2315/16* (2013.01); *B01D 2325/20* (2013.01)

(58) Field of Classification Search
None
See application file for complete search history.

(56) References Cited

U.S. PATENT DOCUMENTS

| 5,827,714 A | 10/1998 | Yamamoto et al. |
| 6,255,094 B1 | 7/2001 | Yamamoto et al. |
| 7,521,212 B1 | 3/2009 | Morgan et al. |
| 7,993,875 B2 | 8/2011 | Yamamoto et al. |
| 8,187,853 B2 | 5/2012 | Yamamoto et al. |
| 8,372,617 B2 | 2/2013 | Yamamoto et al. |
| 10,743,556 B2 | 8/2020 | Puigferrat |
| 2007/0020736 A1 | 1/2007 | Samain |
| 2012/0184015 A1 | 7/2012 | Mine et al. |
| 2016/0215315 A1 | 7/2016 | Dekany et al. |
| 2017/0204443 A1 | 7/2017 | Baumgartner et al. |

FOREIGN PATENT DOCUMENTS

| EP | 0557580 A1 | 9/1993 |
| EP | 1405856 A1 | 4/2004 |
| EP | 0931097 A1 | 9/2005 |
| EP | 2484686 A1 | 8/2012 |
| EP | 2526784 A1 | 11/2012 |
| EP | 2722394 A1 | 4/2014 |
| WO | 9632492 | 10/1996 |
| WO | 9815581 | 4/1998 |
| WO | 9931224 | 6/1999 |
| WO | 0104341 A1 | 1/2001 |
| WO | 2005067962 A2 | 7/2005 |
| WO | 2006034225 A2 | 3/2006 |
| WO | 2007051475 A1 | 5/2007 |

(Continued)

OTHER PUBLICATIONS

Antoine, T. et al., "Highly Efficient Biosynthesis of the Oligosaccharide Moiety of the GD3 Ganglioside by Using Metabolically Engineered *Escherichia coli*," Angew. Chem. Int. Ed., 2005, vol. 44, pp. 1350-1352.

(Continued)

*Primary Examiner* — Suzanne M Noakes
*Assistant Examiner* — Jae W Lee
(74) *Attorney, Agent, or Firm* — Neal, Gerber & Eisenberg LLP

(57) ABSTRACT

This invention relates to a method for the enzymatic synthesis of oligosaccharides, preferably human milk oligosaccharides (HMOs) The method comprises the enzymatic transfer of a glycosyl moiety and subsequent removal of by-products, such as lactose, by nanofiltration using a membrane comprising an active polyamide layer.

20 Claims, No Drawings

(56) References Cited

FOREIGN PATENT DOCUMENTS

| WO | 2007101862 | A1 | 9/2007 |
|---|---|---|---|
| WO | 2010070104 | A | 6/2010 |
| WO | 2010116317 | A1 | 10/2010 |
| WO | 2010142305 | A1 | 12/2010 |
| WO | 2012010889 | A1 | 1/2012 |
| WO | 2012112777 | A2 | 8/2012 |
| WO | 2012156897 | A1 | 11/2012 |
| WO | 2012156898 | A1 | 11/2012 |
| WO | 2012158517 | A | 11/2012 |
| WO | 2013083623 | A1 | 6/2013 |
| WO | 2013185780 | A1 | 12/2013 |
| WO | 2014153253 | A1 | 9/2014 |
| WO | 2014167537 | A1 | 10/2014 |
| WO | 2015036138 | A1 | 3/2015 |
| WO | 2015106943 | A1 | 7/2015 |
| WO | 2015150328 | A1 | 10/2015 |
| WO | 2016008602 | A1 | 1/2016 |
| WO | 2016063262 | A1 | 4/2016 |
| WO | 2016095924 | A1 | 6/2016 |
| WO | 2016157108 | A1 | 10/2016 |
| WO | 2016199069 | A1 | 12/2016 |
| WO | 2016199071 | A1 | 12/2016 |
| WO | 2017086443 | A1 | 5/2017 |

OTHER PUBLICATIONS

Aydogan, N. et al., "Effect of Operating Parameters on the Separation of Sugars by Nanofiltration," Separation Science and Technology, 1998, vol. 33(12), pp. 1767-1785.

Baumgärtner, F. et al., "Construction of *Escherichia coli* strains with chromosomally integrated expression cassettes for the synthesis of 20-fucosyllactose," Microbial Cell Factories, 2013, 13 pages. http://www.microbialcellfactories.com/content/12/1/40.

Cantarel, B.L. et al., "The Carbohydrate-Active EnZymes database (CAZy): an expert resource for Glycogenomics," Nucleic Acids Research, 2009, vol. 37, pp. D233-D238.

Chen, X. (2015)."Human Milk Oligosaccharides (HMOS): Structure, Function, and Enzyme-Catalyzed Synthesis," Elsevier Inc. (vol. 72), Advances in Carbohydrate Chemistry and Biochemistry, pp. 113-190. http://dx.doi.org/10.1016/ps.accb.2015.08.002.

Cobucci-Ponzano, B. et al., "b-Glycosyl Azides as Substrates for a-Glycosynthases: Preparation of Efficient a-L-Fucosynthases," Chemistry & Biology, 2009, vol. 16, pp. 1097-1108.

Córdova, A. et al., "Purification of galacto-oligosaccharides (GOS) by three-stage serial nanofiltration units under critical transmembrane pressure conditions," Chemical Engineering Research and Design, 43 pages, http://dx.doi.org/10.1016/j.cherd.2016.11.006.

Drouillard, S. et al. "Efficient synthesis of 60-sialyllactose, 6,60-disialyllactose, and 60-KDO-lactose by metabolically engineered *E. coli* expressing a multifunctional sialyltransferase from the Photobacterium sp. JT-ISH-224," Carbohydrate Research, 2010, vol. 345, pp. 1394-1399.

Drouillard, S. et al., "Large-Scale Synthesis of H-Antigen Oligosaccharides by Expressing Helicobacter pylori a1,2-Fucosyltransferase in Metabolically Engineered *Escherichia coli* Cells," Angew. Chem. Int. Ed. 2006, vol. 45, pp. 1778-1780.

Fierfort, N. et al., "Genetic engineering of *Escherichia coli* for the economical production of sialylated oligosaccharides," Journal of Biotechnology, 2008, vol. 134, pp. 261-265.

Gilbert, M. et al., The synthesis of sialylated oligosaccharides using CMP-Neu5Ac synthetase/sialyltransferase fusion, Nature Biotechnology, 1998, vol. 16, 99 769-772.

Goulas, A.K. et al., "Fractionation of oligosaccharides by nanofiltration," Journal of the Science of Food and Agriculture, 2003, vol. 83, pp. 675-680.

Goulas, A.K. et al., "Purification of oligosaccharides by nanofiltration," Journal of Membrane Science, 2002, vol. 209, pp. 321-335.

Han, N.S. et al., "Biotechnological production of human milk oligosaccharides," Biotechnology Advances, 2012, vol. 30, pp. 1268-1278.

Lee, W. et al., "Whole cell biosynthesis of a functional oligosaccharide, 2'-fucosyllactose, using engineered *Escherichia coli*," Microbial Cell Factories, 2012, 22 pages. https://doi.org/10.1186/1475-2859-11-48.

Lenntech. (2013) "Biotech Elements; Small Size Spiral-wound Elements for Lab Testing", 2 pages.

Li, W. et al., "Study on nanofiltration for purifying fructo-oligosaccharides: I. Operation modes," Journal of Membrane Science, 2004, vol. 245, pp. 123-129.

Luo, J et al., "An integrated membrane system for the biocatalytic production of 30-sialyllactose from dairy by-products," Bioresource Technology, 2014, vol. 166, pp. 9-16.

Martinez-Ferez, A. et al., "Goats' milk as a natural source of lactose-derived oligosaccharides: Isolation by membrane technology," International Dairy Journal, 2006, vol. 16, pp. 173-181.

Maru, I et al., "Synthesis of Sialyllactose from N-Acetylneuraminic Acid and Lactose by a Neuraminidase from Arthrobacter ureafaciens," Biosci. Biotech. Biochem., 1992, vol. 56(10), pp. 1557-1561.

Masuda, M., et al., "Continuous Production of Sialyllactose from Colominic Acid Using a Membrane Reactor," Journal of Bioscience and Bioengineering, 2000, vol. 89(2), pp. 119-125.

Peirtsegaele, E. (2017) "Nanofiltration: The Newest Class of Membrane Filtration," Microdyn-Nadir US, Inc. 3 pages.

Mine, T. et al., "An α2,3-Sialyltransferase from Photobacterium sp. JT-ISH-224 Transfers N-Acetylneuraminic Acid to Both the O-2 and O-3' Hydroxyl Groups of Lactose," Journal of Carbohydrate Chemistry, 2010, vol. 29, pp. 51-60.

Mine, T. et al., "An a2,6-sialyltransferase cloned from Photobacterium leiognathi strain JT-SHIZ-119 shows both sialyltransferase and neuraminidase activity," Glycobiology, 2010, vol. 20(2), pp. 158-165.

Murata, T. et al., "Facile enzymatic conversion of lactose into lacto-N-tetraose and lacto-N-neotetraose," Glycoconjugate Journal, 1999, vol. 16, pp. 189-195.

Ninonuevo, M.R. et al., "A Strategy for Annotating the Human Milk Glycome," J. Agric. Food Chem., 2006, vol. 54, pp. 7471-7480.

Nordvang, R. T., et al. (2015). Production of prebiotic oligosaccharides by novel enzymatic catalysis. Technical University of Denmark, Department of Chemical and Biochemical Engineering. 142 pages.

Nordvang, R.T. et al., "Separation of 3'-sialyllactose and lactose by nanofiltration: A trade-off between charge repulsion and pore swelling induced by high pH," Separation and Purification Technology, 2014, vol. 138, pp. 77-83.

Osanjo, G. et al., "Directed Evolution of the R-L-Fucosidase from Thermotoga maritima into an R-L- Transfucosidase," Biochemistry, 2007, vol. 46, pp. 1022-1033.

Priem, B. et al., "A new fermentation process allows large-scale production of human milk oligosaccharides by metabolically engineered bacteria," Glycobiology, 2002, vol. 12(4), pp. 235-240.

Sano, M. et al., "An enzyme releasing lacto-N-biose from oligosaccharides," Proc. Natl. Acan. Sci. USA, 1992, vol. 89, pp. 8512-8516.

Sano, M. et al., "Purification and Characterization of an Enzyme Releasing Lacto-N-biose from Oligosaccharides with Type 1 Chain," The Journal of Biological Chemistry, 1993, vol. 268(25), pp. 18560-18566.

Sarney, D.B. et al., "A Novel Approach to the Recovery of Biologically Active Oligosaccharides from Milk Using a Combination of Enzymatic Treatment and Nanofiltration," Biotechnology and Bioengineering, 2000, vol. 69 (4), pp. 461-467.

Shoda, S. et al., "Chemo-enzymatic synthesis of novel oligo-N-acetyllactosamine derivatives having a b(1-4)-b(1-6) repeating unit by using transition state analogue substrate," Cellulose, 2006, vol. 13, pp. 477-484.

Ten Bruggencate, S.J.M. et al, "Functional role and mechanisms of sialyllactose and other sialylated milk oligosaccharides," Nutrition Reviews, 2014, vol. 72(6), pp. 377-389.

Urashima, T. et al. (2011) Nutrition and Diet Research Progress: Milk Oligosaccharides. New York: Nova Science Publishers, Inc. 92 pages.

(56) References Cited

OTHER PUBLICATIONS

Wada, J. et al., "1,2-alpha-L-Fucosynthase: A glycosynthase derived from an inverting alpha-glycosidase with an unusual reaction mechanism," FEBS Letters, 2008, vol. 582, pp. 3739-3743.

Wada, J. et al., "Bifidobacterium bifidum Lacto-N-Biosidase, a Critical Enzyme for the Degradation of Human Milk Oligosaccharides with a Type 1 Structure," Applied and Environmental Microbiology, 2008, vol. 74(13), pp. 3996-4004.

Yamamoto, T. et al., "A β-galactoside α2,6-sialyltransferase produced by a marine bacterium, Photobacterium leiognathi JT-SHIZ-145, is active at pH 8," Glycobiology, 2007, vol. 17(11), pp. 1167-1174.

Yamamoto, T. et al., "Cloning and Expression of a Marine Bacterial β-Galactoside α2,6-Sialyltransferase Gene from Photobacterium damsela JT0160," J. Biochem., 1998, vol. 123, pp. 94-100.

Yushkin, A., et al., "Improvement of MWCO determination by using branched PEGs and MALDI method," Separation and Purification Technology, 2019, vol. 211, pp. 108-116.

Trisep UA60 (retrieved from the Internet <<https://www.microdyn-nadir.com/wp-content/uploadsfTB-003-TRISEP-NADIR-Membrane-Products.pdf>>, retrieved on Apr. 26, 2021) (3 pages).

SYNTHESIS OF OLIGOSACCHARIDES

CROSS-REFERENCE TO RELATED APPLICATION

This application is a continuation of U.S. patent application Ser. No. 16/626,245, now U.S. Pat. No. 11,214,588, filed on Dec. 23, 2019, which is a national stage entry pursuant to 35 U.S.C. § 371 of International Application No. PCT/IB2018/054753, filed on Jun. 27, 2018, which claims priority to each of DK Patent Application No. PA 2017 70522, filed on Jun. 30, 2017, DK Patent Application No. PA 2017 70523, filed on Jun. 30, 2017, and DK Patent Application No. PA 2017 70524, filed on Jun. 30, 2017, the contents of all of which are fully incorporated herein by reference.

FIELD OF THE INVENTION

This invention relates to a method for the enzymatic synthesis of oligosaccharides, preferably human milk oligosaccharides (HMOs).

BACKGROUND OF THE INVENTION

In recent years, the manufacture and commercialization of complex carbohydrates including naturally secreted oligosaccharides have increased significantly due to their roles in numerous biological processes occurring in living organisms. Secreted oligosaccharides such as human milk oligosaccharides (HMOs) are carbohydrates which have gained much interest in recent years and are becoming important commercial targets for nutrition and therapeutic industries. In particular, the synthesis of these HMOs has increased significantly due to the role of HMOs in numerous biological processes occurring in humans. The great importance of HMOs is directly linked to their unique biological activities such as antibacterial, antiviral, immune system and cognitive development enhancing activities. Human milk oligosaccharides are found to act as prebiotics in the human intestinal system helping to develop and maintain the intestinal flora. Furthermore, they have also proved to be anti-inflammatory, and therefore these compounds are attractive components in the nutritional industry for the production of, for example, infant formulas, infant cereals, clinical infant nutritional products, toddler formulas, or as dietary supplements or health functional food for children, adults, elderly or lactating women, both as synthetically composed and naturally occurring compounds and salts thereof. Likewise, the compounds are also of interest in the medicinal industry for the production of therapeutics due to their prognostic use as immunomodulators. However, the syntheses and purification of these oligosaccharides and their intermediates remained a challenging task for science.

The availability of naturally occurring sialylated human milk oligosaccharides is limited from natural sources. Mature human milk is the natural milk source that contains the highest concentrations of milk oligosaccharides (12-14 g/l), other milk sources are cow's milk (0.01 g/l), goat's milk and milk from other mammals. Approximately 200 HMOs have been detected from human milk by means of combination of techniques including microchip liquid chromatography mass spectrometry (HPLC Chip/MS) and matrix-assisted laser desorption/ionization Fourier transform ion cyclotron resonance mass spectrometry (MALDI-FT ICR MS) (Ninonuevo et al. *J. Agric. Food Chem.* 54, 7471 (2006)), from which to date at least 115 oligosaccharides have been structurally determined (Urashima et al.: *Milk Oligosaccharides*, Nova Medical Books, NY, 2011; Chen *Adv. Carbohydr. Chem. Biochem.* 72, 113 (2015)). Due to the large number of similar HMOs and their low concentrations in mammalian milk, isolation of HMOs is a difficult task even in milligram quantities. To date only analytical HPLC methodologies have been developed for the isolation of some HMOs from natural sources. It is therefore difficult to provide suitable HMO replacements in foods, particularly in infant formulae which display at least part of the entire spectrum of HMOs.

Biotechnological approaches have proved to be promising and cost-efficient for the synthesis of a variety of HMOs, especially tri- or tetrasaccharide HMOs. Precisely, those HMOs can be produced in aqueous media by fermentation of genetically modified bacteria, yeasts or other microorganisms. See, for example, WO 01/04341, WO 2007/101862, WO 2010/070104, WO 2010/142305, WO 2012/112777, WO 2014/153253, WO 2015/036138, WO 2015/150328, WO 2016/008602, EP-A-2722394, Priem et al. *Glycobiology* 12, 235 (2002), Drouillard et al. *Angew. Chem. Int. Ed.* 45, 1778 (2006), Han et al. *Biotechnol. Adv.* 30, 1268 (2012), Lee et al. *Microb. Cell Fact.* 11:48 (2012) and Baumgartner et al. *Microb. Cell Fact.* 12:40 (2013).

Efforts have also been made to develop processes for synthesizing enzymatically mixtures of HMO oligosaccharides, see e.g. EP-A-577580, WO 2012/156897, WO 2012/156898, WO 2016/063326, WO 2016/157108 or WO 2016/199071. Such processes have provided reaction mixtures containing a plurality of different oligosaccharides.

Aydogan et al. (*Separ. Sci. Technol.* 33, 1767 (1998)) stated that nanofiltration is not a very suitable method for fractionation of sugars.

WO 98/15581 discloses the retention characteristics of salts and carbohydrates (lactose, sialyllactose, lacto-N-triose II, lacto-N-tetraose), and concludes that while both GE GH and GE GE polyamide membranes allow ions to pass, the GE GE membrane retains sialyllactose or similar trisaccharides more efficiently than the GE GH membrane. No conclusion about whether lactose could be separated from higher oligosaccharides was drawn.

Goulas et al. (*J. Sci. Food Agric.* 83, 675 (2003)) investigated the fractionating of commercial oligosaccharide mixtures by nanofiltration and observed that the rejection and permeate concentration values given by the membranes for the sugars during the filtration of single-sugar solutions would be not the same as if these sugars had been in a mixed solution.

WO 2005/067962 discloses the isolation of goat milk oligosaccharides comprising filtration of skimmed goat milk ultrafiltration permeate with a ceramic membrane of 1-5 kDa. Although a partial separation of salts and lactose is anticipated, the application is silent to quantify this. Nevertheless, the method further comprises active charcoal chromatography, ion exchange chromatography and electrodialysis to remove lactose and salts.

Luo et al. (*Biores. Technol.* 166, 9 (2014)) and Nordvang et al. (*Separ. Purif. Technol.* 138, 77 (2014)) tested the separation of enzymatically produced 3'-SL from lactose by nanofiltration; although a polyethersulphone (PES) membrane with a MWCO of 1000-1400 Da and a sulphonated PES membrane with a MWCO of 600-800 Da were suitable to separate the most of the lactose after diafiltration, the loss of 3'-SL was significant and its purity after separation was rather moderate, thus 3'-SL was further purified with anion exchange chromatography.

Evidence is accumulating that the resident community of microbes, called the microbiome, in the human digestive tract plays a major role in health and disease. When the normal composition of the microbiome is thrown off balance, the human host can suffer consequences. Recent research has implicated microbiome imbalances in disorders as diverse as cancer, obesity, inflammatory bowel disease, psoriasis, asthma, and possibly even autism. HMOs are believed to positively modulate the microbiome, and they are of increasing interest for this purpose. However, the remarkable diversity of HMOs, coupled with their lack of availability, has hampered studies of the specific functions of individual HMOs. The prior art enzymatic reactions, although being able to produce more diversified HMOs, suffer from the fact that the conversion rate is rather moderate and the mixture contains a substantial amount of lactose.

Accordingly, there is a clear need for specific HMOs or combinations of HMOs, without substantial amount of lactose, to modulate the microbiome in a desired manner, so as to address specific human health issues, and/or to produce those HMOs enzymatically in more efficient way.

SUMMARY OF THE INVENTION

The first aspect of the invention provides a method for producing a compound Gly-A by glycosylating acceptor A with a donor Gly-B under the catalysis of a glycosidase capable of transferring the Gly moiety from the donor to the acceptor thereby forming a mixture containing Gly-A, A, Gly-B and B, comprising:
  a) contacting said mixture with a polyamide nanofiltration membrane with a molecular weight cut-off (MWCO) of 600-3500 Da ensuring the retention of Gly-A, A and Gly-B and allowing at least a part of compound B to pass, wherein the $MgSO_4$ rejection of the membrane is 50-90%,
  b) optional diafiltration of the retentate obtained in step a),
  c) and collecting the retentate obtained in step a) or step b) enriched in compound Gly-A,
    wherein A means a tri- or higher oligosaccharide,
    B means a disaccharide,
    Gly means a glycosyl moiety,
    Gly-A means compound A glycosylated with the Gly moiety, and
    Gly-B means compound B glycosylated with the Gly moiety,
    provided that compounds A and Gly-B are not identical.

The second aspect of the invention provides a method for improving the conversion of the product formation of compound Gly-A in an enzymatic reaction wherein acceptor A is glycosylated with a donor Gly-B under the catalysis of a glycosidase capable of transferring the Gly moiety from the donor to the acceptor thereby forming a mixture containing Gly-A, A, Gly-B and B, comprising:
  a) contacting said mixture, under diafiltration condition, with a polyamide nanofiltration membrane with a molecular weight cut-off (MWCO) of 600-3500 Da ensuring the retention of Gly-A, A and Gly-B and allowing at least a part of compound B to pass, wherein the $MgSO_4$ rejection of the membrane is 50-90%,
  b) and collecting the retentate enriched in compound Gly-A,
    wherein A means a tri- or higher oligosaccharide,
    B means a disaccharide,
    Gly means a glycosyl moiety,
    Gly-A means compound A glycosylated with the Gly moiety, and
    Gly-B means compound B glycosylated with the Gly moiety,
    provided that compounds A and Gly-B are not identical.

In both aspects, compound B is preferably lactose.

In both aspects, also preferably, compound A is a tri- to octasaccharide, more preferably a tri-, tetra- or pentasaccharide.

In both aspects, also preferably, the Gly residue is a monosaccharide residue. More preferably, the monosaccharide Gly residue is fucosyl and the glycosidase is a fucosidase, especially a transfucosidase, or the Gly residue is sialyl and the glycosidase is a sialidase, especially a transsialidase.

In both aspects, also preferably, the polyamide nanofiltration membrane is a thin-film composite (TFC) membrane.

In both aspects, yet preferably, the polyamide nanofiltration membrane is a phenylene diamine or a piperazine membrane.

In a preferred embodiment in both aspects, the method comprises diafiltration.

DETAILED DESCRIPTION OF THE INVENTION

Terms and Definitions

The term "monosaccharide" means a sugar of 5-9 carbon atoms that is an aldose (e.g. D-glucose, D-galactose, D-mannose, D-ribose, D-arabinose, L-arabinose, D-xylose, etc.), a ketose (e.g. D-fructose, D-sorbose, D-tagatose, etc.), a deoxysugar (e.g. L-rhamnose, L-fucose, etc.), a deoxy-aminosugar (e.g. N-acetylglucosamine, N-acetylmannosamine, N-acetylgalactosamine, etc.), an uronic acid, a ketoaldonic acid (e.g. sialic acid) or equivalents.

The term "disaccharide" means a carbohydrate consisting of two monosaccharide units linked to each other by an interglycosidic linkage.

The term "tri- or higher oligosaccharide" means a sugar polymer consisting of at least three, preferably from three to eight, more preferably from three to six, monosaccharide units (vide supra). The oligosaccharide can have a linear or branched structure containing monosaccharide units that are linked to each other by interglycosidic linkages.

The term "human milk oligosaccharide" or "HMO" means a complex carbohydrate found in human breast milk (Urashima et al.: *Milk Oligosaccharides*, Nova Medical Books, N Y, 2011; *Chen Adv. Carbohydr. Chem. Biochem.* 72, 113 (2015)). The HMOs have a core structure being a lactose unit at the reducing end that is elongated by one or more β-N-acetyl-lactosaminyl and/or one or more β-lacto-N-biosyl units, and which core structures can be substituted by an α L-fucopyranosyl and/or an α-N-acetyl-neuraminyl (sialyl) moiety. In this regard, the non-acidic (or neutral) HMOs are devoid of a sialyl residue, and the acidic HMOs have at least one sialyl residue in their structure. The non-acidic (or neutral) HMOs can be fucosylated or non-fucosylated. Examples of such neutral non-fucosylated HMOs include lacto-N-triose (LNTri, GlcNAc(β1-3)Gal (β1-4)Glc), lacto-N-tetraose (LNT), lacto-N-neotetraose (LNnT), lacto-N-neohexaose (LNnH), para-lacto-N-neohexaose (pLNnH), para-lacto-N-hexaose (pLNH) and lacto-N-hexaose (LNH). Examples of neutral fucosylated HMOs include 2'-fucosyllactose (2'-FL), lacto-N-fucopentaose I (LNFP-I), lacto-N-difucohexaose I (LNDFH-I), 3-fucosyllactose (3-FL), difucosyllactose (DFL), lacto-N-fucopentaose II (LNFP-II), lacto-N-fucopentaose III (LNFP-III), lacto-N-difucohexaose III (LNDFH-III), fucosyl-lacto-N-hexaose II (FLNH-II), lacto-N-fucopentaose V (LNFP-V), lacto-N-fucopentaose VI (LNFP-VI), lacto-N-difucohexaose II (LNDFH-II), fucosyl-lacto-N-hexaose I (FLNH-I), fucosyl-para-lacto-N-hexaose I (FpLNH-I), fucosyl-para-lacto-N-neohexaose II (F-pLNnH II) and fucosyl-lacto-N-neohexaose (FLNnH). Examples of acidic HMOs include 3'-sialyllactose (3'-SL), 6'-sialyllactose (6'-SL), 3-fucosyl-3'-sialyllactose (FSL), LST a, fucosyl-LST a (FLST a), LST b, fucosyl-LST b (FLST b), LST c, fucosyl-LST c (FLST c), sialyl-LNH (SLNH), sialyl-lacto-N-hexaose (SLNH), sialyl-lacto-N-neohexaose I (SLNH-I), sialyl-lacto-N-neohexaose II (SLNH-II) and disialyl-lacto-N-tetraose (DSLNT).

The term "sialyl" or "sialyl moiety" means the glycosyl residue of sialic acid (N-acetyl-neuraminic acid, Neu5Ac), preferably linked with α-linkage:

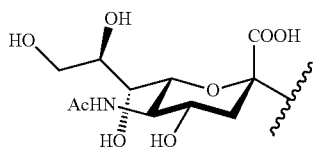

The term "fucosyl" means an L-fucopyranosyl group, preferably linked with α-interglycosidic linkage:

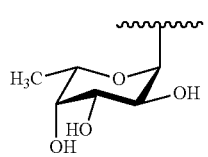

"N-acetyl-glucosaminyl" means an N-acetyl-2-amino-2-deoxy-D-glucopyranosyl (GlcNAc) group, preferably linked with β-linkage:

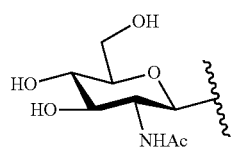

"N-acetyl-lactosaminyl" means the glycosyl residue of N-acetyl-lactosamine (LacNAc, Galpβ1-4GlcNAcp), preferably linked with β-linkage:

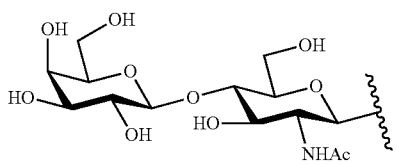

Furthermore, the term "lacto-N-biosyl" means the glycosyl residue of lacto-N-biose (LNB, Galββ1-3GlcNAcp), preferably linked with β-linkage:

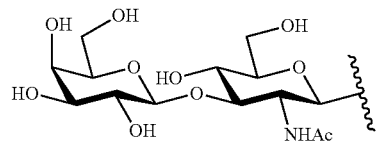

Rejection factor of a salt (in percent) is calculated as $(1-\kappa_p/\kappa_r) \cdot 100$, wherein $\kappa_p$ is the conductivity of the salt in the permeate and $\kappa_r$ is the conductivity of the salt in the retentate. The retentate concentration is practically equal to the feed concentration concerning the salt. The procedure for measuring rejection of salts is disclosed in the working examples below.

Rejection factor of a carbohydrate (in percent) is calculated as $(1-C_p/C_r) \cdot 100$, wherein $C_p$ is the concentration of the carbohydrate in the permeate and $C_r$ is the concentration of the carbohydrate in the retentate. The retentate concentration is practically equal to the feed concentration concerning the carbohydrate. The procedure for measuring rejection of a carbohydrate is disclosed in the examples.

Separation factor concerning two carbohydrates is calculated as $(C_{p1}/C_{r1})/(C_{p2}/C_{r2})$, wherein $C_{p1}$ and $C_{p2}$ are the concentrations of the first and the second carbohydrate, respectively, in the permeate, and Cri and $C_{r2}$ are the concentrations of the first and the second carbohydrate, respectively, in the retentate.

"Pure water flux" is defined as the volume of purified water (e.g. distilled water, RO water) that passes through a membrane per unit time, per unit area and per unit of transmembrane pressure under specified conditions (at 23-25° C., 10 bar and constant cross-flow of 300 l/h). The procedure for measuring the pure water flux is disclosed in example 3 below.

Enzymatic Production of Gly-A

In the enzymatic reactions comprising the utilization of a glycosidase, a glycosyl moiety from a donor molecule is transferred to an acceptor, thereby forming a glycosylated acceptor and the residue of the donor devoid of the glycosyl moiety.

The enzymatic reaction comprising A as acceptor and Gly-B as donor under the catalysis of a glycosidase that is able to transfer the glycosyl residue Gly from the donor to the acceptor, can be depicted as follows:

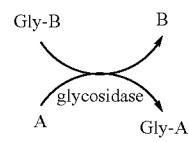

wherein A is a tri- or higher oligosaccharide, Gly is a monosaccharide glycosyl moiety, B is a disaccharide, Gly-B is disaccharide glycosylated with the Gly moiety and Gly-A is compound A glycosylated with the Gly moiety. However, the glycosidases, in general, are able to transfer the Gly residue from the newly formed Gly-A back to the compound B that has previously been produced from Gly-B, therefore reaching an equilibrium: A+Gly-B ⇌ Gly-A+B. In these reactions the conversion rate is rather moderate, meaning the valuable product Gly-A is comprised in the reaction mixture along with A, B and Gly-B.

In order to shift the equilibrium towards the product (Gly-A) formation, one may add any of A and Gly-B in excess, however the reaction mixture thus will contain that particular component in a significant amount, the separation of which from the valuable product Gly-A may be problematic or cumbersome.

Another way to push the equilibrium for formation Gly-A is to (continuously) remove the other product, namely component B, from the reaction mixture.

The present inventors have surprisingly found that component B can be selectively separated (removed) from an aqueous mixture comprising A, B, Gly-A and Gly-B by a nanofiltration step, therefore the conversion rate is significantly increased and the reaction equilibrium is shifted for the product formation of Gly-A so that mixture contains Gly-A in majority.

Accordingly, in a first aspect, a method is provided for producing a compound Gly-A by glycosylating acceptor A with a donor Gly-B under the catalysis of a glycosidase capable of transferring the Gly moiety from the donor to the acceptor thereby forming a mixture containing Gly-A, A, Gly-B and B, comprising:
a) contacting said mixture with a nanofiltration membrane with a molecular weight cut-off (MWCO) of 600-3500 Da ensuring the retention of Gly-A, A and Gly-B and allowing at least a part of compound B to pass, wherein the active (top) layer of the membrane is composed of polyamide, and wherein the $MgSO_4$ rejection of the membrane is 50-90%,
b) optional diafiltration of the retentate obtained in step a),
c) and collecting the retentate obtained in step a) or step b) enriched in compound Gly-A,
wherein A means a tri- or higher oligosaccharide,
B means a disaccharide,
Gly means a glycosyl moiety,
Gly-A means compound A glycosylated with the Gly moiety, and
Gly-B means compound B glycosylated with the Gly moiety,
provided that compound A and Gly-B are not identical.

In a second aspect, a method is provided for improving the conversion of the product formation of compound Gly-A in an enzymatic reaction wherein acceptor A is glycosylated with a donor Gly-B under the catalysis of a glycosidase capable of transferring the Gly moiety from the donor to the acceptor thereby forming a mixture containing Gly-A, A, Gly-B and B, comprising:
a) contacting said mixture, under diafiltration condition, with a nanofiltration membrane with a molecular weight cut-off (MWCO) of 600-3500 Da ensuring the retention of Gly-A, A and Gly-B and allowing at least a part of compound B to pass, wherein the active (top) layer of the membrane is composed of polyamide, and wherein the $MgSO_4$ rejection of the membrane is 50-90%,
b) and collecting the retentate enriched in compound Gly-A,
wherein A means a tri- or higher oligosaccharide,
B means a disaccharide,
Gly means a glycosyl moiety,
Gly-A means compound A glycosylated with the Gly moiety, and
Gly-B means compound B glycosylated with the Gly moiety,
provided that compound A and Gly-B are not identical.

The term "ensuring the retention of Gly-A, A and Gly-B" preferably means that, during the nanofiltration step, Gly-A, A and Gly-B do not pass, or at least significantly do not pass, through the membrane and thus their vast majority will be present in the retentate. The term "allowing at least a part of compound B to pass through the membrane" preferably means, that compound B, at least partially, can penetrate the membrane and be collected in the permeate. In the first aspect of the invention, in case of high rejection (about 90%) of compound B, a subsequent diafiltration with pure water may be necessary to bring all or at least the majority of compound B in the permeate. The higher the rejection of compound B the more diafiltration water is necessary for efficient separation.

The term "contacting said mixture, under diafiltration condition, with a nanofiltration membrane" preferably means that the nanofiltration is carried out so that water is continuously added to the retentate and passed through the membrane. In doing so, all or at least the majority of compound B can be removed from the retentate and brought to the permeate.

The applied nanofiltration membrane shall be tight for Gly-A, A and Gly-B in order that they are efficiently retained. Preferably, the rejection of Gly-A, A and Gly-B is more than 95%, more preferably 97%, even more preferably 99%. Membranes with MWCO of more than 3500 Da are expected to allow more or significant amount of Gly-A, A and Gly-B pass through the membrane thus show a reduced retention of Gly-A, A and Gly-B and therefore are not suitable for the purposes of the invention, and can be excluded. In the same time, membranes with MWCO of less than 600 Da can also be excluded, because—together with the retention of Gly-A, A and Gly-B—that of the mono- and disaccharides is also expected, meaning that the overall separation of the compounds would likely be poor. In this regard, it is preferred that the rejection of the disaccharide (compound B) is not more than 80-90%. If the disaccharide rejection turns to be 90±1-2%, the rejection of at least Gly-A shall preferably be around 99% or higher in order to achieve a practically satisfying separation.

It has been found that the above requirements are simultaneously fulfilled when the membrane is relatively loose for $MgSO_4$, that is its rejection is about 50-90%. In this regard the above specified membrane is tight for Gly-A, A and Gly-B, and loose for mono- and disaccharides, and as well as for $MgSO_4$. Therefore, it is possible to separate e.g. lactose, which is a precursor in making human milk oligosaccharides enzymatically or by fermentation, from the human milk oligosaccharides product by nanofiltration with a good efficacy, and additionally a substantial part of divalent ions also passes to the permeate. In some embodiments, the $MgSO_4$ rejection factor is 60-90%, 70-90%, 50-80%, 50-70%, 60-70% or 70-80%. Preferably, the $MgSO_4$ rejection factor on said membrane is 80-90%.

Also preferably, the membrane has a rejection factor for NaCl that is lower than that for $MgSO_4$. In one embodiment, the rejection factor for NaCl is not more than 50%. In other embodiment, the rejection factor for NaCl is not more than 40%. In other embodiment, the rejection factor for NaCl is not more than 30%. In this latter embodiment, a substantial reduction of all monovalent salts in the retentate is also achievable.

Also preferably, the membrane has a rejection factor for NaCl that is lower than that for $MgSO_4$. In one embodiment, the rejection factor for NaCl is not more than 50%. In other embodiment, the rejection factor for NaCl is not more than 40%. In other embodiment, the rejection factor for NaCl is not more than 30%. In this latter embodiment, a substantial reduction of all monovalent salts in the retentate is also achievable.

Also preferably, in some embodiments, the pure water flux of the membrane is at least 50 l/m²h. Preferably, the pure water flux of the membrane is at least 60 l/m²h, at least 70 l/m²h, at least 80 l/m²h or at least 90 l/m²h.

The active or the top layer of nanofiltration membrane suitable for the purpose of the invention is preferably made of polyamide. Although membranes of different type seem to have promising separation efficacy, for example NTR-7450 having sulphonated PES as active layer for separating lactose and 3'-SL (Luo et al. (*Biores. Technol.* 166, 9 (2014); Nordvang et al. (*Separ. Purif Technol.* 138, 77 (2014)), the above specified membrane used in the invention shows always better separation of lactose from an HMO. In addition, the above mentioned NTR-7450 membrane is subject to fouling, which typically results in a drop in flux, increasing the lactose rejection and therefore a reduced separation factor (see examples).

Yet preferably, the polyamide membrane is a polyamide with phenylene diamine or piperazine building blocks as amine, more preferably piperazine (referred to as piperazine-based polyamide, too).

Yet preferably, the membrane suitable for the purpose of the present invention is a thin-film composite (TFC) membrane.

An example of suitable piperazine based polyamide TFC membranes is TriSep® UA60.

The claimed method applies a nanofiltration membrane characterized by some or all of the above features and thus one or more of the following benefits are provided: selectively and efficiently removes compound B, a disaccharide, preferably lactose, from compounds Gly-A, A and Gly-B which are tri- or higher oligosaccharides, preferably HMOs, thereby yielding an enriched Gly-A, A and Gly-B fraction and/or improving conversion of Gly-A; removes efficiently monovalent as well as divalent salts therefore no ion exchange step is necessary or, if desalination is still needed, the ion exchange treatment requires substantially less resin; higher flux during the nanofiltration can be maintained compared to other membranes used for the same or similar purpose in the prior art, which reduces the operation time; the membrane applied in the claimed method is less prone to getting clogged compared to the prior art solutions; the membrane applied in the claimed can be cleaned and regenerated completely therefore can be recycled without substantial reduction of its performance.

The nanofiltration membrane defined in the method of the invention is more beneficial compared to the prior art membranes used for the same or similar purpose as that of the present invention. Specifically, polyvinylidene fluoride (PVDF) membrane of Luo et al. or Nordvang et al. (ETNA01PP, MWCO: 1000 Da, Alfa Laval) rejects tri- to hexasaccharides less efficiently and the separation factor over lactose is substantially lower; sulphonated PES membrane of Luo et al. or Nordvang et al. (NTR-7450, MWCO: 600-800, Nitto-Denko), besides showing lower separation factor of tri- to hexasaccharides over lactose, gets easily clogged; GE GE (polyamide, MWCO: 1000 Da) and GE GH (polyamide, MWCO: 2500 Da) membranes of WO 98/15581, besides showing lower separation factor of tri- to hexasaccharides over lactose, operate at lower flux and retain higher amount of salts in the permeate due to high NaCl rejection factor.

Accordingly, in one embodiment of the first aspect of the invention, a method is provided for producing a compound Gly-A by glycosylating acceptor A with a donor Gly-B under the catalysis of a glycosidase capable of transferring the Gly moiety from the donor to the acceptor thereby forming a mixture containing Gly-A, A, Gly-B and B, comprising:

a) contacting said mixture with a piperazine-based polyamide nanofiltration membrane with a molecular weight cut-off (MWCO) of 1000-3500 Da ensuring the retention of Gly-A, A and Gly-B and allowing at least a part of compound B to pass through the membrane, wherein the $MgSO_4$ rejection factor on said membrane is 80-90%, and wherein
    the NaCl rejection factor on said membrane is lower than that for $MgSO_4$, and/or
    the pure water flux value of said membrane is at least 50 l/m²h,
  b) a subsequent optional diafiltration of the retentate obtained in step a),
  c) and collecting the retentate obtained in step a) or step b) enriched in compound Gly-A.

In one embodiment of the second aspect, a method is provided for improving the conversion of the product formation of compound Gly-A in an enzymatic reaction wherein acceptor A is glycosylated with a donor Gly-B under the catalysis of a glycosidase capable of transferring the Gly moiety from the donor to the acceptor thereby forming a mixture containing Gly-A, A, Gly-B and B, comprising:

a) contacting said mixture, under diafiltration condition, with a nanofiltration membrane with a molecular weight cut-off (MWCO) of 1000-3500 Da ensuring the retention of Gly-A, A and Gly-B and allowing at least a part of compound B to pass, wherein the active (top) layer of the membrane is composed of polyamide, and wherein the $MgSO_4$ rejection of the membrane is 80-90%, and wherein
    the NaCl rejection factor on said membrane is lower than that for $MgSO_4$, and/or
    the pure water flux value of said membrane is at least 50 l/m²h,
  b) and collecting the retentate enriched in compound Gly-A.

Preferably, in the above embodiments, the NaCl rejection factor of the membrane is at most the half of the $MgSO_4$ rejection factor.

To achieve all the benefits mentioned above, the nanofiltration membrane to be applied in both aspects of the invention, preferably:
  is a piperazine-based polyamide membrane with a MWCO of 1000-3500 Da,
  has a $MgSO_4$ rejection of 50-90%, preferably 80-90%,
  has a NaCl rejection of not more than 30%, and
  has a pure water flux value of at least 50 l/m²h, preferably 90 l/m²h.

Improvement of the conversion of the enzymatic synthesis means that the molar ratio of Gly-A is increased compared to that in the equilibrium before the selective removal of disaccharide B takes place. In an equilibrium A+Gly-B ⇌ Gly-A+B, the conversion of Gly-A is calculated as the fraction of the molar concentration of Gly-A and that of the acceptor A or donor Gly-B in percent depending on which one was added to the reaction mixture in lower amount. The method of the invention increases the conversion, compared to that in the equilibrium before removal of compound B, by at least 10%, preferably by at least 25%, more preferably by at least 50%, even more preferably by at least 75%, particularly by at least 100%.

Also in a preferred embodiment, compound B is lactose and compound Gly-B (serving as donor in the above disclosed enzymatic reaction) is a glycosylated lactose wherein the Gly residue is attached to the lactose by an interglycosidic linkage. The Gly residue is preferably a monosaccharide residue, therefore Gly-B is a trisaccharide.

Also preferably, compound A (serving as acceptor in the above disclosed enzymatic reaction) is a tri- or higher oligosaccharide, more preferably tri- to hexasaccharides. Accordingly, Gly-A (being as the intended product in the above disclosed enzymatic reaction) is a glycosylated compound A, that is a glycosylated tri- or higher oligosaccharide. In a further preferred embodiment, the Gly residue is a monosaccharide residue, therefore Gly-A is a tetra- or higher oligosaccharide, more preferably tetra- to heptasaccharide.

In the enzymatic reaction disclosed above an enzyme capable of transferring the Gly residue from Gly-B to compound A is utilized. Such an enzyme comprises a glycosidase activity, preferably a transglycosidase activity thereby transferring a glycosyl moiety (e.g. a sialyl moiety, a fucosyl moiety, an N-acetyllactosaminyl moiety, a lacto-N-biosyl moiety, etc.) and forming a new bond between the transferred glycosyl moiety and the acceptor molecule (compound A) at a specific position of the acceptor.

According to a more preferred embodiment, compound B is lactose and Gly is
  fucosyl (thus Gly-B is a fucosyllactose, particularly 2'-FL or 3-FL),
  sialyl (thus Gly-B is a sialyllactose, particularly 3'-SL or 6'-SL),
  N-acetylglucosaminyl (thus Gly-B is a N-acetylglucosaminyllactose, particularly lacto-N-triose II),
  lacto-N-biosyl (thus Gly-B is a lacto-N-biosyl lactose, particularly LNT), or
  N-acetyllactosaminyl (thus Gly-B is a N-acetyllactosaminyl lactose, particularly LNnT);
and a suitable glycosidase is a fucosidase (when Gly is fucosyl), a sialidase (when Gly is sialyl), a N-acetyl-hexosaminidase (when Gly is N-acetylglucosaminyl), a lacto-N-biosidase (when Gly is lacto-N-biosyl) or N-acetyl-lactosaminidase (when Gly is N-acetyllactosaminyl).

Also more preferably, compound A is characterized by formula 1 or formula 2:

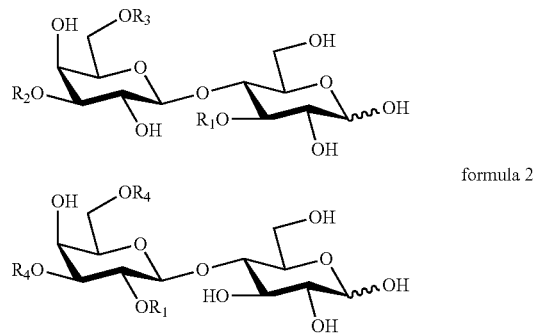

formula 1 formula 2 wherein $R_1$ is fucosyl or H,
$R_2$ is selected from N-acetyl-lactosaminyl and lacto-N-biosyl groups, wherein the N-acetyl lactosaminyl group may carry a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, $R_3$ is H or N-acetyl-lactosaminyl group optionally substituted with a glycosyl residue comprising one or more N-acetyl-lactosaminyl and/or one or more lacto-N-biosyl groups; any N-acetyl-lactosaminyl and lacto-N-biosyl group can be substituted with one or more sialyl and/or fucosyl residue, and
each $R_4$ independently is sialyl or H,
with the proviso that at least one of $R_1$ or $R_4$ is not H;
and within the scope of formula 1, compound A can be characterized by formula 1a or formula 1b:

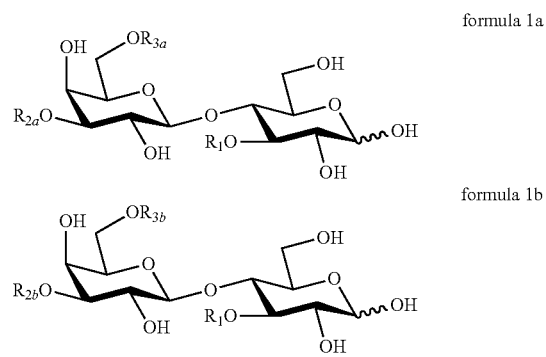

formula 1a formula 1b wherein $R_1$ is as defined above,
$R_{2a}$ is an N-acetyl-lactosaminyl group optionally substituted with a glycosyl residue comprising one N-acetyl-lactosaminyl and/or one lacto-N-biosyl group; any N-acetyl-lactosaminyl and lacto-N-biosyl group can be substituted with one or more sialyl and/or fucosyl residue, but preferably void of a sialyl and/or fucosyl residue,
$R_{3a}$ is H or an N-acetyl-lactosaminyl group optionally substituted with a lacto-N-biosyl group; any N-acetyl-lactosaminyl and lacto-N-biosyl group can be substituted with one or more sialyl and/or fucosyl residue, but preferably void of a sialyl and/or fucosyl residue,
$R_{2b}$ is a lacto-N-biosyl group optionally substituted with sialyl and/or fucosyl residue, but preferably void of a sialyl and/or fucosyl residue, and
$R_{3b}$ is H or an N-acetyl-lactosaminyl group optionally substituted with one or two N-acetyl-lactosaminyl and/or one lacto-N-biosyl group; any N-acetyl-lactosaminyl and lacto-N-biosyl group can be substituted with one or more sialyl and/or fucosyl residue, but preferably without a sialyl and/or fucosyl residue;
and preferably, the compounds of formulae 1a and 1b have one or more of the following linkages and modifications:
  the N-acetyl-lactosaminyl group in the glycosyl residue of $R_{2a}$ in formula 1a is attached to another N-acetyl-lactosaminyl group by a 1-3 interglycosidic linkage,
  the lacto-N-biosyl group in the glycosyl residue of $R_{2a}$ in formula 1a is attached to the N-acetyl-lactosaminyl group by a 1-3 interglycosidic linkage,
  the lacto-N-biosyl group in the glycosyl residue of $R_{3a}$ in formula 1a is attached to the N-acetyl-lactosaminyl group by a 1-3 interglycosidic linkage,
  the N-acetyl-lactosaminyl group in the glycosyl residue of $R_{3b}$ in formula 1b is attached to another N-acetyl-lactosaminyl group by a 1-3 or 1-6 interglycosidic linkage, and
  the lacto-N-biosyl group in the glycosyl residue of $R_{3b}$ in formula 1b is attached to the N-acetyl-lactosaminyl group by a 1-3 interglycosidic linkage.

Preferably, compound A defined above is further characterized in that:

if present, the fucosyl residue attached to the N-acetyl-lactosaminyl and/or the lacto-N-biosyl group is linked to
- the galactose of the lacto-N-biosyl group with a 1-2 interglycosidic linkage and/or
- the N-acetyl-glucosamine of the lacto-N-biosyl group with a 1-4 interglycosidic linkage and/or
- the N-acetyl-glucosamine of the N-acetyl-lactosaminyl group with a 1-3 interglycosidic linkage, if present, the sialyl residue attached to the N-acetyl-lactosaminyl and/or the lacto-N-biosyl group is linked to
- the galactose of the lacto-N-biosyl group with a 2-3 interglycosidic linkage and/or
- the N-acetyl-glucosamine of the lacto-N-biosyl group with a 2-6 interglycosidic linkage and/or
- the galactose of the N-acetyl-lactosaminyl group with a 2-6 interglycosidic linkage.

According to a further preferred embodiments of compound A, a compound according to general subformulae 1a, 1b or 2 may be:

a trisaccharide such as 2'-O-fucosyllactose (2'-FL), 3-O-fucosyllactose (3-FL), 3'-O-sialyllactose (3'-SL), a tetrasaccharide such as lacto-N-tetraose (LNT), lacto-N-neotetraose (LNnT), a pentasaccharide such as lacto-N-fucopentaose I (LNFP-I, Fucα1-2Galβ1-3GlcNAcβ1-3Galβ1-4Glc), Galβ1-4GlcNAcβ1-3Galβ1-4[Fucα1-3]Glc, lacto-N-fucopentaose II (LNFP-II, Galβ1-3[Fucα1-4]GlcNAcβ1-3Galβ1-4Glc), lacto-N-fucopentaose III (LNFP-III, Galβ1-4[Fucα1-3]GlcNAcβ1-3Galβ1-4Glc), lacto-N-fucopentaose V (LNFP-V, Galβ1-3GlcNAcβ1-3Galβ1-4[Fucα1-3]Glc), lacto-N-fucopentaose VI (LNFP-VI, Galβ1-4GlcNAcβ1-3Galβ1-4[Fucα1-3]Glc), Galβ1-4GlcNAcβ1-3Galβ1-4[Fucα1-3]Glc, LST a (NeuAcα2-3Galβ1-3GlcNAcβ1-3Galβ1-4Glc), LST b (Galβ1-3[NeuAcα2-6]GlcNAcβ1-3Galβ1-4Glc), LST c (NeuAcα2-6Galβ1-4GlcNAcβ1-3Galβ1-4Glc), Galβ1-4GlcNAcβ1-3Galβ1-4[Fucα1-3]Glc, a hexasaccharide such as lacto-N-hexaose (LNH, Galβ1-3GlcNAcβ1-3[Galβ1-4GlcNAcβ1-6]Galβ1-4Glc), lacto-N-neohexaose (LNnH, Galβ1-4GlcNAcβ1-3[Galβ1-4GlcNAcβ1-6]Galβ1-4Glc), para-lacto-N-hexaose (pLNH, Galβ1-3GlcNAcβ1-3Galβ1-4GlcNAcβ1-3Galβ1-4Glc), para-lacto-N-neohexaose (pLNnH, Galβ1-4GlcNAcβ1-3Galβ1-4GlcNAcβ1-3Galβ1-4Glc), disialyl-LNT (DSLNT, NeuAcα2-3Galβ1-3[NeuAcα2-6]GlcNAcβ1-3Galβ1-4Glc), LNDFH II (Galβ1-3[Fucα1-4]GlcNAcβ1-3Galβ1-4[Fucα1-3]Glc), Galβ1-3[Neu5Acα2-6][Fucα1-4]GlcNAcβ1-3Galβ1-4Glc, Galβ1-3[Neu5Acα2-6]GlcNAcβ1-3Galβ1-4[Fucα1-3]Glc, LNDFH III (Galβ1-4[Fucα1-3]GlcNAcβ1-3Galβ1-4[Fucα1-3]Glc, a heptasaccharide such as fucosyl-LNH I (FLNH-I, Fucα1-2Galβ1-3GlcNAcβ1-3[Galβ1-4GlcNAcβ1-6]Galβ1-4Glc), fucosyl-LNH II (FLNH-II, Galβ1-4[Fucα1-3]GlcNAcβ1-6[Galβ1-3GlcNAcβ1-3]Galβ1-4Glc), fucosyl-para-LNH I (FpLNH-I, Galβ1-3GlcNAcβ1-3Galβ1-4[Fucα1-3]GlcNAcβ1-3Galβ1-4Glc), fucosyl-para-LNH II (FpLNH-II, Galβ1-3[Fucα1-4]GlcNAcβ1-3Galβ1-4GlcNAcβ1-3Galβ1-4Glc), Galβ1-4GlcNAcβ1-3Galβ1-4[Fucα1-3]GlcNAcβ1-3Galβ1-4Glc, Galβ1-4[Fucα1-3]GlcNAcβ1-3Galβ1-4GlcNAcβ1-3Galβ1-4Glc, sialyl-LNH (SLNH, Galβ1-3GlcNAcβ1-3[NeuAcα2-6Galβ1-4GlcNAcβ1-6]Galβ1-4Glc), sialyl-LNnH I (SLNnH-I, Galβ1-4GlcNAcβ1-3[NeuAcα2-6Galβ1-4GlcNAcβ1-6]Galβ1-4Glc), sialyl-LNnH II (SLNnH-II, Galβ1-4GlcNAcβ1-6[NeuAcα2-6Galβ1-4GlcNAcβ1-3]Galβ1-4Glc), Fucα1-2Galβ1-3GlcNAcβ1-3[Galβ1-4GlcNAcβ1-6]Galβ1-4Glc, Galβ1-3[Fucα1-4]GlcNAcβ1-3[Galβ1-4GlcNAcβ1-6]Galβ1-4Glc, Galβ1-4[Fucα1-3]GlcNAcβ1-6[Galβ1-4GlcNAcβ1-3]Galβ1-4Glc, NeuAcα2-3Galβ1-3GlcNAcβ1-3[Galβ1-4GlcNAcβ1-6]Galβ1-4Glc, an octasaccharide such as difucosyl-LNH I (DFLNH-I, Galβ1-4[Fucα1-3]GlcNAcβ1-6[Fucα1-2Galβ1-3GlcNAcβ1-3]Galβ1-4Glc), difucosyl-para-LNH (DFpLNH, Galβ1-3[Fucα1-4]GlcNAcβ1-3Galβ1-4[Fucα1-3]GlcNAcβ1-3Galβ1-4Glc), difucosyl-para-LNnH (DFpLNnH, Galβ1-4[Fucα1-3]GlcNAcβ1-3Galβ1-4[Fucα1-3]GlcNAcβ1-3Galβ1-4Glc), lacto-N-octaose (LNO, Galβ1-3GlcNAcβ1-3[Galβ1-4GlcNAcβ1-3Galβ1-4GlcNAcβ1-6]Galβ1-4Glc), lacto-N-neooctaose (LNnO, Galβ1-4GlcNAcβ1-3[Galβ1-3GlcNAcβ1-3Galβ1-4GlcNAcβ1-6]Galβ1-4Glc), iso-lacto-N-octaose (iLNO, Galβ1-3GlcNAcβ1-3[Galβ1-3GlcNAcβ1-3Galβ1-4GlcNAcβ1-6]Galβ1-4Glc), para-lacto-N-octaose (pLNO, Galβ1-3GlcNAcβ1-3Galβ1-4GlcNAcβ1-3Galβ1-4GlcNAcβ1-3Galβ1-4Glc), fucosyl-sialyl-LNH (FSLNH, NeuAcα2-3Galβ1-3GlcNAcβ1-3[Galβ1-4[Fucα1-3]GlcNAcβ1-6]Galβ1-4Glc), fucosyl-sialyl-LNH II (FSLNH-II, Fucα1-2Galβ1-3GlcNAcβ1-3[NeuAcα2-6Galβ1-4GlcNAcβ1-6]Galβ1-4Glc), disialyl-LNH I (DSLNH-I, NeuAcα2-6Galβ1-4GlcNAcβ1-6[NeuAcα2-3Galβ1-3GlcNAcβ1-3]Galβ1-4Glc), disialyl-LNH II (DSLNH-II, Galβ1-4GlcNAcβ1-6[NeuAcα2-3Galβ1-3[NeuAcα2-6]GlcNAcβ1-3]Galβ1-4Glc), disialyl-LNnH (DSLNnH, NeuAcα2-6Galβ1-4GlcNAcβ1-6[NeuAcα2-6Galβ1-4GlcNAcβ1-3]Galβ1-4Glc), Fucα1-2Galβ1-3[Fucα1-4]GlcNAcβ1-3[Galβ1-4GlcNAcβ1-6]Galβ1-4Glc, Fucα1-2Galβ1-4[Fucα1-3]GlcNAcβ1-6[Galβ1-4GlcNAcβ1-3]Galβ1-4Glc, NeuAcα2-3Galβ1-3[Fucα1-4]GlcNAcβ1-3[Galβ1-4GlcNAcβ1-6]Galβ1-4Glc, NeuAcα2-6Galβ1-4[Fucα1-3]GlcNAcβ1-3[Galβ1-4GlcNAcβ1-6]Galβ1-4Glc, Galβ1-4[Fucα1-3]GlcNAcβ1-3[NeuAcα2-6Galβ1-4GlcNAcβ1-6]Galβ1-4Glc.

In one embodiment, the glycosidase is a fucosidase. Fucosidases (classified in EC 3.2.1.38 and 3.2.1.51) are widespread in living organisms such as mammals, plants, fungi and bacteria. These enzymes belong to the families 29, 35 and 95 of the glycoside hydrolases (GH29, GH35 and GH95) as defined by the CAZY nomenclature (http://www.cazy.org; Cantarel et al. *Nucleic Acids Res.* 37, D233 (2009)). Fucosidases from GH29 are retaining enzymes (3D structure: $(\beta/\alpha)_8$) whereas fucosidases from GH95 are inverting enzymes (3D structure: $(\alpha/\alpha)_6$). The substrate specificity of the GH29 family is broad whereas that of the GH95 family is strict to α1,2-linked fucosyl residues. The GH29 family seems to be divided into two subfamilies. One subfamily typically has strict specificity towards α1,3- and α1,4-fucosidic linkages. The members of a further subfamily have broader specificity, covering all α-fucosyl linkages. Fucosidases generally hydrolyse the terminal fucosyl residue from glycans. However these enzymes are able to act as catalyst for fucosylation reaction due to their transfucosylation activity under kinetically controlled conditions.

The utility of glycosidases, including fucosidases, has benefited from various engineering techniques.

In the technique of "rational engineering", novel altered enzymes (mutants) are created by point mutation. The mutation generally affects the active site of the enzyme. Replacement of a catalytic nucleophilic residue with a non-nucleophilic residue results in the formation of an inactive mutant or an altered enzyme with reduced transglycosylation activity due the lack of appropriate environment for the formation of the reactive host-guest complex for transglycosylation. However, in the presence of a more active fucosyl donor than the natural one, the mutated enzyme is able to transfer efficiently the fucose residue to a suitable acceptor. Such a mutant glycosidase is termed glycosynthase. Rational engineering of enzymes generally requires reliance on the static 3D protein structure. By means of rational engineering, an α-1,2-L-fucosynthase from *Bifidobacterium bifidum* and efficient α-L-fucosynthases from *Sulfolobus solfataricus* and *Thermotoga maritima* with acceptor dependent regioselectivity have recently been developed and provided [Wada et al. *FEBS Lett.* 582, 3739 (2008), Cobucci-Ponzano et al. *Chem. Biol.* 16, 1097 (2009)]. These altered enzymes are devoid of product hydrolysis activity.

A second technique of "directed evolution" involves random mutagenesis of a selected natural glycosidase enzyme to create a library of enzyme variants, each of which is altered in a single position or in multiple positions. The variants can be inserted into suitable microorganisms such as *E. coli* or *S. cerevisiae* for producing recombinant variants with slightly altered properties. Clones expressing improved enzyme variants are then identified with a fast and reliable screening method, selected and brought into a next round of mutation process. The recursive cycles of mutation, recombination and selection are continued until mutant(s) with the desired activity and/or specificity is/are evolved. An α-L-fucosidase from *Thermotoga maritima* has recently been converted into an efficient α-L-transfucosidase by directed evolution [G. Osanjo et al. *Biochemistry* 46, 1022 (2007)]. The cited article describes the cloning, mutation, screening, recombination and protein purification steps in detail.

It is envisaged that transfucosidase and/or fucosynthase enzyme mutants retaining transfucosidase activity and having a sequence similarity/homology to the sequence of the known and published enzyme sequences, such as that of the α-L-transfucosidase of G. Osanjo et al, of at least 70%, such as 75%, preferably 80%, such as 85% can be used in the present invention. Preferably, the sequence similarity is at least 90%, more preferably 95%, 97%, 98% or most preferably 99%.

Engineered transfucosidases and fucosynthases possess a broader donor and acceptor specificity than the wild types of fucosidases and fucosyltransferases and so can be used in a particularly wide variety of reactions. The engineered enzymes are, therefore, more advantageous for industrial use.

In one particular embodiment, the fucosidase is α1,3/4-fucosidase or a α1,3/4-transfucosidase, that is those wild type or engineered fucosidases that are able to transfer a fucose residue to the 3-position of the glucose in an acceptor of formula 2, to the 3-position of the N-acetyl-glucosamine in a, preferably terminal, N-acetyl-lactosaminyl group in an acceptor of formula 1, 1a or 1b, or to the 4-position of the N-acetyl-glucosamine in a, preferably terminal, lacto-N-biosyl group, in an acceptor of formula 1, 1a or 1b. In this regard, the preferred compounds of Gly-A obtainable by α1,3/4-fucosylation of a suitable acceptor are DFL, SFL, LNFP-II, LNFP-III, LNDFH-I, LNDFH-II, LNDFH-III, FLNH-II, Galβ1-4[Fucα1-3]GlcNAcβ1-3[Galβ1-4GlcNAcβ1-6]Galβ1-4Glc, Galβ1-4GlcNAcβ1-3[Galβ1-4[Fucα1-3]GlcNAcβ1-6]Galβ1-4Glc, FpLNH-I, FpLNH-II, DFpLNH, Galβ1-4GlcNAcβ1-3Galβ1-4[Fucα1-3]GlcNAcβ1-3Galβ1-4Glc, Galβ1-4[Fucα1-3]GlcNAcβ1-3Galβ1-4GlcNAcβ1-3Galβ1-4Glc, DFpLNH, DFpLNH, DFpLNnH, DFpLNnH, DFLNH-I, DFLNH-II, DFLNnH, DFLNnH, TFLNH, TFpLNnH, TFpLNH-II, FLST a, FLST c, FSLNH-III, FSLNnH-I, DFSLNH-I, DFSLNH-III, FDSLNT-I, FDSLNH-II, FDSLNH-III and FDSLNnH, The α1,3/4-transfucosidase is preferably selected from α-L-fucosidases as classified according to EC 3.2.1.111, having transfucosidase activity, such as the α1,3/4 fucosidase from *Bifidobacterium longum* subsp. *infantis* ATCC 15697 as set forth in U.S. Pat. No. 8,361,756 as protein of SEQ ID No. 18 and other fucosidases which have at least 60%, preferably at least 70%, more preferably at least 80%, particularly at least 90%, identity with amino acid positions 56 to 345 of the α1,3/4 fucosidase from *Bifidobacterium longum* subsp. *infantis* ATCC 15697. Examples of such other fucosidases are listed below in Table 1.

TABLE 1

| Description | Accession No. |
|---|---|
| α-L-fucosidase [*Bifidobacterium longum* subsp. *infantis* EK3] | KEY30716.1 |
| α-L-fucosidase [*Bifidobacterium longum*] | WP_013140205.1 |
| putative α1,3/4 fucosidase [*Bifidobacterium kashiwanohense* JCM 15439] | KFI63931.1 |
| putative α1,3/4 fucosidase [*Bifidobacterium scardovii*] | KFI94501.1 |
| α-L-fucosidase [*Gardnerella vaginalis*] | WP_004574432.1 |
| α-L-fucosidase [*Gardnerella vaginalis*] | WP_019261748.1 |
| hypothetical protein [*Gardnerella vaginalis*] | WP_020759655.1 |
| α-L-fucosidase [*Gardnerella vaginalis*] | WP_009993891.1 |
| α-L-fucosidase [*Gardnerella vaginalis*] | WP_004573610.1 |
| α-L-fucosidase [*Gardnerella vaginalis*] | WP_004120276.1 |
| α-L-fucosidase [*Gardnerella vaginalis*] | WP_004114072.1 |
| α-L-fucosidase [*Gardnerella vaginalis*] | WP_004137675.1 |
| α-L-fucosidase [*Gardnerella vaginalis*] | WP_014554869.1 |
| α-L-fucosidase [*Bifidobacterium bifidum* CAG:234] | WP_022173522.1 |
| α-L-fucosidase [*Actinomyces* sp. ICM47] | WP_009647833.1 |
| hypothetical protein [*Streptomyces ipomoeae*] | WP_009295550.1 |
| α-L-fucosidase [*Actinomyces* sp. oral taxon 180] | WP_009211856.1 |
| hypothetical protein [*Actinomyces* sp. oral taxon 172] | WP_021611755.1 |
| α-L-fucosidase [*Bifidobacterium* sp. 7101] | WP_029678277.1 |
| hypothetical protein [*Actinomyces* sp. HPA0247] | WP_016461038.1 |
| α-L-fucosidase [*Actinomyces* sp. ICM54] | EWC96238.1 |

TABLE 1-continued

| Description | Accession No. |
|---|---|
| α-L-fucosidase [*Actinomyces odontolyticus*] | WP_003795385.1 |
| α-L-fucosidase [*Atopobium* sp. ICM58] | WP_009055210.1 |
| α-L-fucosidase [*Paenibacillus* sp. J14] | WP_028538247.1 |
| α-L-fucosidase [*Actinomyces odontolyticus*] | WP_003792781.1 |
| α1,3/4 fucosidase [*Propionibacterium acidipropionici*] | WP_015071771.1 |
| α-L-fucosidase [*Propionibacterium acidipropionici*] | WP_028700846.1 |
| hypothetical protein [*Paenibacillus barengoltzii*] | WP_016312877.1 |
| α-L-fucosidase [*Actinomyces* sp. ICM39] | WP_007588699.1 |
| α-L-fucosidase [*Propionibacterium jensenii*] | WP_028703334.1 |
| α-L-fucosidase [*Lactobacillus shenzhenensis*] | WP_022529554.1 |
| hypothetical protein [*Paenibacillus* sp. HW567] | WP_019912449.1 |
| putative α-1 3/4-fucosidase [*Clostridium hathewayi* CAG:224] | WP_022032399.1 |
| α-fucosidase [*Clostridium hathewayi*] | WP_006775425.1 |
| α-L-fucosidase [*Janibacter* sp. HTCC2649] | WP_009776262.1 |
| α-fucosidase [*Clostridium phytofermentans*] | WP_012201036.1 |
| α-L-fucosidase [*Enterococcus gallinarum*] | WP_029486307.1 |
| uncharacterized protein [*Blautia* sp. CAG:237] | WP_022215646.1 |
| MULTISPECIES: α-L-fucosidase [*Enterococcus*] | WP_005470131.1 |
| α-L-fucosidase [*Enterococcus gallinarum* EG2] | EEV33648.1 |
| α-L-fucosidase [*Ruminococcus* sp. CAG:60] | CCY33010.1 |
| α-L-fucosidase [*Ruminococcus* sp. CAG:9] | WP_022380664.1 |
| α-fucosidase [*Blautia wexlerae*] | WP_025580031.1 |
| α-fucosidase [*Ruminococcus* sp. 5_1_39BFAA] | WP_008706707.1 |
| α-fucosidase [*Paenibacillus* sp. HGF5] | WP_009593620.1 |
| α-L-fucosidase [*Paenibacillus* sp. FSL H8-457] | ETT68114.1 |
| hypothetical protein [*Clostridium hathewayi*] | WP_002604401.1 |
| hypothetical protein [*Paenibacillus* sp. PAMC 26794] | WP_017691196.1 |
| α-L-fucosidase [*Paenibacillus* sp. FSL R5-192] | ETT29638.1 |
| α-fucosidase [*Paenibacillus* sp. Y412MC10] | WP_015736742.1 |
| α-L-fucosidase [*Paenibacillus alvei*] | WP_021262981.1 |
| α-fucosidase [*Paenibacillus* sp. UNC217MF] | WP_028532504.1 |
| α-fucosidase [*Paenibacillus alvei*] | WP_005546194.1 |
| α-L-fucosidase [*Paenibacillus alvei*] | WP_021254840.1 |
| hypothetical protein [*Paenibacillus terrigena*] | WP_018756045.1 |
| α-fucosidase [*Ruminococcus obeum*] | WP_005422251.1 |
| α-L-fucosidase [*Paenibacillus* sp. FSL H7-689] | ETT43086.1 |
| α-fucosidase [*Paenibacillus lactis*] | WP_007127626.1 |
| α-fucosidase [*Bacillus* sp. J13] | WP_028406965.1 |
| hypothetical protein [*Paenibacillus daejeonensis*] | WP_020617104.1 |
| hypothetical protein [*Clostridium* sp. KLE 1755] | WP_021638714.1 |
| α-fucosidase [*Clostridium* sp. ASBs410] | WP_025233568.1 |
| α-fucosidase [*Paenibacillus vortex*] | WP_006211772.1 |
| α-L-fucosidase [*Paenibacillus* sp. FSL R5-808] | ETT35249.1 |
| α-fucosidase [*Clostridium celerecrescens*] | KEZ90324.1 |
| α-L-fucosidase [*Firmicutes bacterium* CAG:94] | WP_022336739.1 |
| α-fucosidase [*Clostridiales bacterium* VE202-27] | WP_025488431.1 |
| α-fucosidase [*Paenibacillus pasadenensis*] | WP_028597616.1 |
| MULTISPECIES: α-fucosidase [*Paenibacillus*] | WP_024629466.1 |
| α-fucosidase [*Paenibacillus* sp. UNC451MF] | WP_028551519.1 |
| α-fucosidase [*Paenibacillus* sp. PAMC 26794] | WP_026081066.1 |
| α-fucosidase [*Paenibacillus* sp. JDR-2] | WP_015843379.1 |
| MULTISPECIES: α-fucosidase [*Clostridiales*] | WP_009250084.1 |
| α-fucosidase [*Clostridium saccharolyticum*] | WP_013273060.1 |

In other particular embodiment, the fucosidase is α1,2-fucosidase or a α1,2-transfucosidase, that is those wild type or engineered fucosidases that are able to transfer a fucose residue to the 2-position of the galactose in an acceptor of formula 2, or to the 3-position of the galactose of the lacto-N-biosyl group an acceptor of formula 1, 1a or 1b. In this regard, the preferred compounds of Gly-A obtainable by α1,2-fucosylation of a suitable acceptor are difucosyllactose, lacto-N-fucopentaose I, lacto-N-difuco-hexaose I, F-LNH I, DF-LNH I, F-LST b and FS-LNH.

More preferably, the enzyme having α1,2-fucosidase and/or α1,2-trans-fucosidase activity may be selected from α-L-fucosidases derived from *Thermotoga maritima* MSB8, *Sulfolobus solfataricus* β2, *Bifidobacterium bifidum* JCM 1254, *Bifidobacterium bifidum* JCM 1254, *Bifidobacterium longum* subsp. *infantis* ATCC 15697, *Bifidobacterium longum* subsp. *infantis* ATCC 15697, *Bifidobacterium longum* subsp. *Infantis* JCM 1222, *Bifidobacterium bifidum* PRL2010, *Bifidobacterium bifidum* S17, *Bifidobacterium longum* subsp *longum* JDM 301, *Bifidobacterium dentium* Bd1, or *Lactobacillus casei* BL23, etc.

Even more preferably the enzyme having α1,2-fucosidase and/or α1,2-trans-fucosidase activity may be selected from following α-L-fucosidases as defined according to the following deposit numbers: gi|4980806 (*Thermotoga maritima* MSB8), gi|13816464 (*Sulfolobus solfataricus* β2), gi|34451973 (*Bifidobacterium bifidum* JCM 1254), gi|242345155 (*Bifidobacterium bifidum*, JCM 1254), gi|213524647 (*Bifidobacterium longum* subsp. *infantis*, ATCC 15697), gi|213522629 (*Bifidobacterium longum* subsp. *infantis* ATCC 15697), gi|213522799 (*Bifidobacterium longum* subsp. *infantis* ATCC 15697), gi|213524646 (*Bifidobacterium longum* subsp. *infantis* ATCC 15697), gi|320457227 (*Bifidobacterium longum* subsp. *infantis* JCM 1222), gi|320457408 (*Bifidobacterium longum* subsp. *infantis* JCM 1222), gi|320459369 (*Bifidobacterium longum* subsp. *infantis* JCM 1222), gi|320459368 (*Bifidobacterium longum* subsp. *infantis* JCM 1222), gi|310867039 (*Bifidobacterium bifidum* PRL2010), gi|310865953 (*Bifidobacterium bifidum* PRL2010), gi|309250672 (*Bifidobacterium bifidum* S17), gi|309251774 (*Bifidobacterium bifidum* S17), gi|296182927 (*Bifidobacterium longum* subsp *longum* JDM 301), gi|296182928 (*Bifidobacterium longum* subsp *longum* JDM 301), gi|283103603 (*Bifidobacterium dentium* Bd1), gi|190713109 (*Lactobacillus casei* BL23), gi|190713871 (*Lactobacillus casei* BL23), gi|190713978 (*Lactobacillus casei* BL23), etc., or a sequence exhibiting a sequence identity with one of the above mentioned enzyme sequences having α1,2-fucosidase and/or α1,2-trans-fucosidase activity of at least 70%, more preferably at least 80%, equally more preferably at least 85%, even more preferably at least 90% and most preferably at least 95% or even 97%, 98% or 99% as compared to the entire wild type sequence on amino acid level.

In other embodiment, the glycosidase is a sialidase. Sialidases (EC 3.2.1.18), classified in the GH33 family, are retaining enzymes with the ability of hydrolysing α-linkage of the terminal sialic acid, mainly those bound to galactose with α-2,3 or α-2,6 linkage, of various sialoglycoconjugates. They are found particularly in diverse virus families and bacteria, and also in protozoa, some invertebrates and mammalian. Some bacterial sialidases can be used to scavenge sialic acids from sialylated glycoprotein, glycolipids or other glycoconjugates for nutriment for bacterial cell growth.

Although sialidases are characterized by their hydrolytic activity, under appropriate reaction condition they are able to catalyse the transfer of sialic acid unit to an asialo acceptor by transsialylation reaction giving rise to the formation of sialoglycoconjugates. Sialidases from pathogen bacteria or viruses such as *Bacteroides fragilis*, *Clostridium* species (e.g. *C. perfringens*), *Corynebacterium diphteriae*, *Haemophilus parasuis*, *Pasteurella multocida*, *Pseudomonas aeruginosa*, *Salmonella typhimurium*, *Streptococcus pneumoniae*, *Tannerella forsythia*, *Vibrio cholerae* or Newcastle disease virus and from non-pathogen ones such as *Actinomyces viscosus*, *Arthrobacter* species or *Micromonospora viridifaciens* are capable to act as catalyst for sialylation reaction due to their transsialidase activity with α-2,3 and/or α-2,6 selectivity. As to the regioselectivity, the ratio between the α-2,3- and α-2,6-linked products varies depending on the enzymes and/or the acceptors. For example sialidases from *A. ureafaciens*, *C. perfringens* and *V. cholerae* have good α-2,6 selectivity, whereas those from *S. typhimurium* and Newcastle disease virus have good to excellent preference to form α-2,3 linkage.

Recently, sialidases from *Bifidobacterium bifidum* and *Bifidobacterium longum* subsp. *infantis* have been identified, cloned and characterized. These sialidases can cleave and so recognize both α-2,3- and α-2,6-linked sialosides. Sialidases from *Bifidobacterium longum* subsp. *infantis* have a consistent preference for α-2,6-linkage whereas sialidases from *Bifidobacterium bifidum* have a consistent preference for α-2,3-linkage.

In order to improve regioselectivity and/or conversion of the transsialylation reaction the sialidases may be subjected to alteration by various engineering techniques (see above).

In one particular embodiment, the sialidase is an α2,3-sialidase or an α2,3-transsialidase, that is those wild type or engineered sialidases that are able to transfer a sialyl residue to the 3-position of the galactose in an acceptor of formula 2, or to the 3-position of the galactose in a terminal lacto-N-biosyl group in an acceptor of formula 1, 1a or 1b. In this regard, the preferred compounds of Gly-A obtainable by α2,3-sialylation of a suitable acceptor are Neu5Acα2-3Galβ1-4(Fucα1-3)Glc (3-O-fucosyl-3'-O-sialyl-lactose), Neu5Acα2-3Galβ1-3GlcNAcβ1-3Galβ1-4Glc (LST a), Neu5Acα2-3Galβ1-4GlcNAcβ1-3Galβ1-4Glc, Neu5Acα2-3Galβ1-3(Fucα1-4)GlcNAcβ1-3Galβ1-4Glc (FLST a), Neu5Acα2-3Galβ1-4(Fucα1-3)GlcNAcβ1-3Galβ1-4Glc, Neu5Acα2-3Galβ1-3GlcNAcβ1-3Galβ1-4(Fucα1-3)Glc, Neu5Acα2-3Galβ1-3(Fucα1-4)GlcNAcβ1-3Galβ1-4(Fucα1-3)Glc, Neu5Acα2-3Galβ1-3(Neu5Acα2-6)GlcNAcβ1-3Galβ1-4Glc (DSLNT), Neu5Acα2-3Galβ1-3(Neu5Acα2-6)(Fucα1-4)GlcNAcβ1-3Galβ1-4Glc (FDSLNT I), Neu5Acα2-3Galβ1-3(Neu5Acα2-6)GlcNAcβ1-3Galβ1-4(Fucα1-3)Glc (FDSLNT II).

The α2,3-transsialidase suitable in the processes of this invention is preferably the α2,3-transsialidase from *Trypanosoma cruzi* (TcTS). However, the α2,3-transsialidases from other microorganisms, such as *T. rangeli*, *T. brucei gambiense*, *T. brucei rhodesiense*, *T. brucei brucei*, *T. congolense* and *Corynebacterium diphtheriae* as described in WO 2012/156898, as well as the α2,3-transsialidases from *Salmonella typhimurium*, *Bacteroides fragilis*, Newcastle disease virus and *Vibrio cholera*, can be used. Moreover, other α2,3-transsialidases can also be used which have at least 60%, preferably at least 70%, more preferably at least 80%, particularly at least 90%, identity with the α2,3-transsialidase from *T. cruzi*. Also preferably, the α2,3-transsialidase may be selected from sialidases or transsialidases as defined according to the following deposit numbers: gi|213524659 (*Bifidobacterium longum* subsp. *infantis* ATCC 15697), gi|213523006 *Bifidobacterium longum* subsp. *infantis* ATCC 15697), gi|309252191 (*Bifidobacterium bifidum* S17), gi|309252190 (*Bifidobacterium bifidum* S17), gi|310867437 (*Bifidobacterium bifidum* PRL2010), gi|310867438 (*Bifidobacterium bifidum* PRL2010), gi|224283484 (*Bifidobacterium bifidum* NCIMB 41171), gi|224283485 (*Bifidobacterium bifidum* NCIMB 41171), gi|334283443 (*Bifidobacterium bifidum* JCM1254), gi|47252690 (*T. cruzi*), gi|432485 (*T. cruzi*).

In other particular embodiment, the sialidase is an α2,6-sialidase or an α2,6-transsialidase, that is those wild type or engineered sialidases that are able to transfer a sialyl residue to the 6-position of the galactose in a terminal N-acetyllactosaminyl group in an acceptor of formula 1, 1a or 1b, or to the 6-position of the N-acetylglucosamine in a, preferably terminal, lacto-N-biosyl group in an acceptor of formula 1, 1a or 1b. In this regard, the preferred compounds of Gly-A obtainable by α2,6-sialylation of a suitable acceptor are LST c, FLST c, SLNH, SLNnH-I, SLNnH-II, FSLNH, FSLNH-III, FSLNnH-I, FSLNnH-II, DFSLNH-I, DFSLNnH, DSLNH-I, DSLNnH, DSLNnH, FDSLNH-III, FDSLNnH, FDSLNnH, TSLNH.

The α2,6-transsialidase suitable in the process of this invention can be any wild type enzyme having α2,6-transsialidase activity, such as an α2,6-sialyl transferase from *Photobacterium damselae* JT0160 (U.S. Pat. Nos. 5,827,714, 6,255,094, Yamamoto et al. *J. Biochem.* 123, 94 (1998)), *Photobacterium* sp. JT-ISH-224 (U.S. Pat. Nos. 7,993,875, 8,187,838, Tsukamoto et al. *J. Biochem.* 143, 187 (2008)) *P. leiognathi* JT-SHIZ-145 (U.S. Pat. Nos. 8,187,853, 8,372,617, Yamamoto et al. *Glycobiology* 17, 1167 (2007)) or *P. leiognathi* JT-SHIZ-119 (US 2012/184016, Mine et al. *Glycobiology* 20, 158 (2010)). The preferred wild type α2,6-sialyl transferases with a substantially identical amino acid sequence with SEQ ID No. 1, that is having at least about 60 percent sequence identity (determined by BLAST) with SEQ ID No. 1, are listed in Table 2.

TABLE 2

| Description | Identity | Accession Number |
|---|---|---|
| α2,6-sialyl transferase [*Photobacterium leiognathi*] | 100% | BAI49484.1 |
| α2,6-sialyl transferase [*Photobacterium leiognathi*] | 96% | BAF91416.1 |
| Chain A, crystal structure of sialyl transferase from *Photobacterium damselae*, residues 113-497 | 70% | 4R9V_A |
| sialyl transferase 0160 [*Photobacterium damselae*] | 68% | WP_005298232.1 |
| Chain A, crystal structure of sialyl transferase from *Photobacterium damselae* | 67% | 4R83_A |
| sialyl transferase 0160 [*Photobacterium damselae*] | 66% | BAA25316.1 |

Preferably, α2,6-sialyl transferases with a substantially identical amino acid sequence with SEQ ID No. 1 that can be mutated to have an α2,6-transsialidase activity with improved regioselectivity, are the sialyl transferase from *P. leiognathi* JT-SHIZ-119 or its Δ2-15 truncated variant, the sialyl transferase from *P. leiognathi* JT-SHIZ-145 or its Δ2-15 truncated variant, or the sialyl transferase from *P. damselae* JT0160 or its Δ2-15 truncated variant, more preferably the sialyl transferase from *P. leiognathi* JT-SHIZ-119 or its Δ2-15 truncated variant. Especially preferred α2,6-transsialidases obtained by enzyme engineering are disclosed in WO 2016/199069.

In other embodiment, the glycosidase is a lacto-N-biosidase or trans-lacto-N-biosidase, that is those wild type or engineered lacto-N-biosidases that are able to transfer a lacto-N-biosyl residue to the 3-position of the galactose of lactose, to the 3-position of the galactose in a terminal N-acetyllactosaminyl group in an acceptor of formula 1, 1a or 1b, or to the 3-position of the galactose in a terminal lacto-N-biosyl group in an acceptor of formula 1, 1a or 1b. In this regard, the preferred compounds of Gly-A obtainable by β1,3-lacto-N-biosylation of a suitable acceptor are lacto-N-hexaose (LNH, Galβ1-3GlcNAcβ1-3(Galβ1-4GlcNAcβ1-6)Gal 1-4Glc), para-lacto-N-hexaose (para-LNH, Galβ1-3GlcNAcβ1-3Galβ1-4GlcNAcβ1-3Galβ1-4Glc), para-lacto-N-hexaose II (para-LNH II, Galβ1-3GlcNAcβ1-3Galβ1-3GlcNAcβ1-3Galβ1-4Glc), lacto-N-octaose (LNO, Galβ1-3GlcNAcβ1-3(Galβ1-4GlcNAcβ1-3Galβ1-4GlcNAcβ1-6)Galβ1-4Glc), iso-lacto-N-octaose (iso-LNO, Galβ1-3GlcNAcβ1-3(Galβ1-3GlcNAcβ1-3Galβ1-4GlcNAcβ1-6)Galβ1-4Glc), para-lacto-N-octaose (para-LNO, Galβ1-3GlcNAcβ1-3Galβ1-4GlcNAcβ1-3Galβ1-4GlcNAcβ1-3Galβ1-4Glc).

Enzymes having a lacto-N-biosidase or trans-lacto-N-biosidase activity are preferably selected from a lacto-N-biosidase or trans-lacto-N-biosidase (EC 3.2.1.140) as classified according to the GH20 family. Lacto-N-biosidases typically proceed through a retaining mechanism. Only two lacto-N-biosidases from *Streptomyces* and *Bifidobacterium bifidum* have been described and characterized up to now, which may be utilized in the present invention as a lacto-N-biosidase or trans-lacto-N-biosidase (see Sano et al., *Proc. Natl. Acad. Sci. USA*, 89, 8512 (1992); Sano et al., *J. Biol. Chem.* 268, 18560 (1993); Wada et al., *Appl. Environ. Microbiol.* 74, 3996 (2008)). Lacto-N-biosidases specifically hydrolyse the terminal lacto-N-biosyl residue (β-D-Gal-(1→3)-D-GlcNAc) from the non-reducing end of oligosaccharides with the structure β-D-Gal-(1→3)-β-D-GlcNAc-(1→3)-β-D-Gal-(1→R). Wada et al. (supra) and Murata et al. (*Glycoconj. J.* 16, 189 (1999)) also demonstrated the ability of the lacto-N-biosidase from *Bifidobacterium bifidum* and *Aureobacterium* sp. L-101, respectively, to catalyse the transglycosylation by incubating donor substrates (such as lacto-N-tetraose and pNP-β-LNB) with acceptors (such as various 1-alkanols and lactose).

Even more preferably, the at least one enzyme having a lacto-N-biosidase or trans-lacto-N-biosidase activity may be selected from lacto-N-biosidases or trans-lacto-N-biosidases derived from *Bifidobacterium bifidum* JCM1254, *Bifidobacterium bifidum* PRL2010, *Bifidobacterium bifidum* NCIMB 41171, *Aureobacterium* sp. L-101 or *Streptomyces* sp., etc.

Even more preferably the at least one enzyme having a lacto-N-biosidase or trans-lacto-N-biosidase activity may be selected from lacto-N-biosidases or trans-lacto-N-biosidases as defined according to the following deposit numbers: gi|167369738 (*Bifidobacterium bifidum* JCM1254), gi|4096812 (*Streptomyces* sp.), gi|310867103 (*Bifidobacterium bifidum* PRL2010), gi|313140985 (*Bifidobacterium bifidum* NCIMB 41171), etc., or a sequence exhibiting a sequence identity with one of the above mentioned enzyme sequences having a lacto-N-biosidase or trans-lacto-N-biosidase activity of at least 70%, more preferably at least 80%, equally more preferably at least 85%, even more preferably at least 90% and most preferably at least 95% or even 97%, 98% or 99% as compared to the entire wild type sequence on amino acid level.

In other embodiment, the glycosidase is an N-acetyllactosaminidase or trans-N-acetyllactosaminidase, that is those wild type or engineered N-acetyllactosaminidases that are able to transfer a N-acetyllactosaminyl residue to the 3-position of the galactose of lactose, or to the 3-position of the galactose in a terminal N-acetyllactosaminyl group in an acceptor of formula 1, 1a or 1b. In this regard, the preferred compounds of Gly-A obtainable by β1,3-N-acetyllactosaminylation of a suitable acceptor are lacto-N-neohexaose (LNnH, Galβ1-4GlcNAcβ1-3(Galβ1-4GlcNAcβ1-6)Galβ1-4Glc), para-lacto-N-neohexaose (para-LNnH, Galβ1-4GlcNAcβ1-3Galβ1-4GlcNAcβ1-3Galβ1-4Glc), lacto-N-neooctaose (LNnO, Galβ1-4GlcNAcβ1-3(Galβ1-3GlcNAcβ1-3Galβ1-4GlcNAcβ1-6)Galβ1-4Glc).

Enzymes having a N-acetyllactosaminidase or trans-N-acetyllactosaminidase activity are preferably selected from a N-acetyllactosaminidase or trans-N-acetyllactosaminidase as described in the following, e.g. lacto-N-biosidases (EC 3.2.1.140) as classified according to the GH20 family. Particularly preferably, chitinase from *bacillus circulans*, more preferably chitinase A1 from *Bacillus Circulans* WL-12 as deposited under gi|142688, may be used as a N-acetyllactosaminidase or trans-N-acetyllactosaminidase, or a sequence exhibiting a sequence identity with one of the above mentioned enzyme sequences having a N-acetyllactosaminidase or trans-N-acetyllactosaminidase activity of at least 70%, more preferably at least 80%, equally more preferably at least 85%, even more preferably at least 90% and most preferably at least 95% or even 97%, 98% or 99% as compared to the entire wild type sequence on amino acid level. Notably, Shoda et al. showed that chitinase A1 from

*B. circulans* WL-12 is able to transfer N-acetyllactosamine with a β-1,6 glycosidic linkage using 1,2-oxazoline derivative of N-acetyllactosamine (Cellulose, 13, 477 (2006)).

In one embodiment, Gly-B is 3-O-fucosyllactose (3-FL), A is lacto-N-tetraose (LNT), Gly-A is lacto-N-fucopentaose II (LNFP-II), and the glycosidase is an α1,3/4-(trans)fucosidase.

In other embodiment, Gly-B is 3-O-fucosyllactose (3-FL), A is lacto-N-neotetraose (LNnT), Gly-A is lacto-N-fucopentaose III (LNFP-III), and the glycosidase is an α1,3/4-(trans)fucosidase.

In other embodiment, Gly-B is 3-O-fucosyllactose (3-FL), A is lacto-N-fucopentaose I (LNFP-I), Gly-A is lacto-N-difucohexaose I (LNDFH-I), and the glycosidase is an α1,3/4-(trans)fucosidase.

In other embodiment, Gly-B is 3-O-fucosyllactose (3-FL), A is lacto-N-fucopentaose V (LNFP-V), Gly-A is lacto-N-difucohexaose II (LNDFH-II), and the glycosidase is an α1,3/4-(trans)fucosidase.

In other embodiment, Gly-B is 3-O-fucosyllactose (3-FL), A is lacto-N-fucopentaose VI (LNFP-VI), Gly-A is lacto-N-difucohexaose I (LNDFH-III), and the glycosidase is an α1,3/4-(trans)fucosidase.

In other embodiment, Gly-B is 3-O-fucosyllactose (3-FL), A is 2'-O-fucosyllactose (2'-FL), Gly-A is difucosyllactose (DFL), and the glycosidase is an α1,3/4-(trans)fucosidase.

In other embodiment, Gly-B is 2'-O-fucosyllactose (2'-FL), A is 3-O-fucosyllactose (3-FL), Gly-A is difucosyllactose (DFL), and the glycosidase is an α1,2-(trans)fucosidase.

In other embodiment, Gly-B is 3'-O-sialyllactose (3'-SL), A is 3-O-fucosyllactose (3-FL), Gly-A is 3-O-fucosyl-3'-O-sialyllactose (FSL), and the glycosidase is an α2,3-transsialidase.

In other embodiment, Gly-B is 3-O-fucosyllactose (3-FL), A is 3'-O-sialyllactose (3'-SL), Gly-A is 3-O-fucosyl-3'-O-sialyllactose (FSL), and the glycosidase is an α1,3/4-(trans)fucosidase.

In other embodiment, Gly-B is 3'-O-sialyllactose (3'-SL), A is lacto-N-tetraose (LNT), Gly-A is LST a, and the glycosidase is an α2,3-transsialidase.

In other embodiment, Gly-B is 3'-O-sialyllactose (3'-SL), A is lacto-N-fucopentaose II (LNFP-II), Gly-A is FLST a, and the glycosidase is an α2,3-transsialidase.

In other embodiment, Gly-B is 6'-O-sialyllactose (6'-SL), A is lacto-N-neotetraose (LNnT), Gly-A is LST c, and the glycosidase is an α2,6-(trans)sialidase.

In other embodiment, Gly-B is 6'-O-sialyllactose (6'-SL), A is lacto-N-fucopentaose VI (LNFP-VI), Gly-A is FLST c, and the glycosidase is an α2,6-(trans)sialidase.

In other embodiment, Gly-B is 3-O-fucosyllactose (3-FL), A is para-lacto-N-neohexaose (pLNnH), Gly-A is a fucosylated pLNnH, and the glycosidase is an α1,3/4-(trans)fucosidase.

In other embodiment, Gly-B is 6'-O-sialyllactose (6'-SL), A is para-lacto-N-neohexaose (pLNnH), Gly-A is a sialylated pLNnH, and the glycosidase is an α2,6-(trans)sialidase.

Also in a preferred embodiment, the separation factor of disaccharide B over a tri- or higher oligosaccharide Gly-A, A or Gly-B is more than 5, preferably more than 10, more preferably more than 25, even more preferably more than 100. Especially, the separation factor of lactose over a human milk oligosaccharide Gly-A is more than 10, preferably more than 25, more preferably more than 50, even more preferably more than 100.

Yet preferably, the separation factor of disaccharide B over a trisaccharide A or Gly-B is more than 5, preferably more than 10, more preferably more than 25. Especially, the separation factor of lactose over 3'-SL or 6'-SL is more than 20, preferably more than 50.

Yet preferably, the separation factor of disaccharide B over a tetrasaccharide A or Gly-A is more than 25, preferably more than 50, more preferably more than 100. Especially, the separation factor of lactose over LNT or LNnT is more than 30, more preferably more than 50.

Yet preferably, the separation factor of disaccharide B over a penta- or hexasaccharide A or Gly-A is more than 100. Especially, the separation factor of lactose over LNFP-I, LNFP-II, LNFP-III, LNFP-V, LNFP-VI, LST a, LST c, FLST a, FLST c, LNDFH-I, LNDFH-II or LNDFH-III is more than 150, more preferably more than 250.

The method of the invention can be conducted under conditions used for conventional nanofiltration with tangential flow or cross-flow filtration with positive pressure compared to permeate side followed by, optionally, diafiltration where both operations could be performed in a batch mode or preferably in continuous mode. The optional diafiltration is conducted by adding pure water to the retentate after the nanofiltration step disclosed above and continuing the filtration process. Conducting diafiltration helps to remove the continuously forming lactose from the reactor more efficiently, therefore shifts the enzymatic equilibrium towards the product formation.

The pH of the feed solution applied for the NF separation according to the present invention is, preferably, not higher than 7, more preferably between 3 and 7, even more preferably around 4 and 5. A low pH may adversely influence the membrane and the solute properties. Nevertheless, the pH shall be in a range under which the (trans)glycosidase is capable of performing the transfer of the Gly moiety from the donor to the acceptor.

The convenient temperature range applied is between 10 and 60° C. Higher temperature provides a higher flux and thus accelerates the process. The membrane is expected to be more open for flow-through at higher temperatures, however this doesn't change the separation factors significantly. On the other hand, since the enzymatic reaction and the continuous removal of the lactose take place parallelly, the preferred temperature range for conducting the nanofiltration separation according to the invention is that under which the (trans)glycosidase is capable of performing the transfer of the Gly moiety from the donor to the acceptor. It is, in general, 20-40° C., however in case of thermostable enzyme the temperature may be as high as 50° C.

A preferred applied pressure in the nanofiltration separation is about 2-50 bar, such as 10-40 bar, the higher the pressure the higher the flux.

In the first aspect of the invention, preferably, the enzymatic reaction is conducted in an enzymatic membrane reactor (see e.g. Luo et al. (*Biores. Technol.* 166, 9 (2014)) composed of the membrane defined, so that compounds Gly-B (donor), A (acceptor) and Gly-A (product) remain in the reactor ("retentate") since they are all tri- or higher oligosaccharides, while compound B as the leaving group of the donor and being a disaccharide can penetrate through the membrane to the permeate fraction. In such membrane reactor, the equilibrium of the enzymatic reaction can be shifted towards the product formation, thus a better conversion is achievable compared to the conventional reactors.

In the second aspect of the invention, both conventional and membrane reactors can be applied, however the enzymatic mixture comprising compounds Gly-B (donor), A (acceptor), Gly-A (product) and B, after reaching a certain conversion or equilibrium, is contacted with the nanofiltration membrane under diafiltration mode using pure water. In doing so, the enzymatic reaction keeps going because the disaccharide B is continuously removed through the membrane to the permeate fraction and its reduced concentration shifts the equilibrium towards its production together with the production of Gly-A which remains in the retentate.

In the final step of the method of invention, the mixture of A, Gly-A and Gly-B (and optionally B if it remains in a small amount) in solid form can then be isolated from the aqueous solution obtained as retentate after UF/DF in a conventional manner, first separating the enzyme from the retentate followed by e.g. by evaporation, spray-drying drying, or lyophilisation. Gly-A can be isolated in pure form from mixture of A, Gly-A and Gly-B (and optionally B) by conventional separation method such as gel chromatography, reversed-phase chromatography, ion exchange chromatography or ligand exchange chromatography.

EXAMPLES

Example 1—Determination of the Rejection Factor of a Substance on a Membrane The NaCl and MgSO$_4$ rejection on a membrane is determined as follows: in a membrane filtration system, a NaCl (0.1%) or a MgSO$_4$ (0.2%) solution is circulated across the selected membrane sheet (for Tami: tubular module) while the permeate stream is circulated back into the feed tank. The system is equilibrated at 10 bars and 25° C. for 10 minutes before taking samples from the permeate and retentate. The rejection factor is calculated from the measured conductivity of the samples: $(1-\kappa_p/\kappa_r) \cdot 100$, wherein $\kappa_p$ is the conductivity of MgSO$_4$ in the permeate and $\kappa_r$ is the conductivity of NaCl or MgSO$_4$ in the retentate.

| membrane | active layer | MWCO | NaCl rej. factor | | MgSO$_4$ rej. factor | |
|---|---|---|---|---|---|---|
| | | | supplier spec. | lab. measurement | supplier spec. | lab. measurement |
| Trisep UA60 | piperazine-PA | 1000-3500 | — | 10% | 80% | 81-89% |
| GE GH | PA | 2500 | — | 81% | — | 76% |
| NTR-7450 | sulph. PES | 600-800 | 50% | 56% | — | 32% |

A carbohydrate rejection factor is determined in a similar way with the difference that the rejection factor is calculated from the concentration of the samples (determined by HPLC): $(1-C_p/C_r) \cdot 100$, wherein $C_p$ is the concentration of the carbohydrate in the permeate and $C_r$ is the concentration of the carbohydrate in the retentate.

Example 2—LST c Production Catalysed by an α2,6-Transsialidase with Continuous Lactose Removal 6'-SL Na-salt (80.0 g) and LNnT (60.0 g) were dissolved in deionized water (860 g), and the pH was adjusted to 5.0 with few drops of acetic acid. α2,6-Transsialidase (A218Y-N222R-G349S-S412β-D451K mutant of *P. leiognathi* JT-SHIZ-119 sialyl transferase truncated by its signal peptide (Δ2-15), the positions of mutations are according to SEQ ID No. 1, see WO 2016/199069) was added in two portions (50 mg at the start and 100 mg after 4 hrs) and the obtained solution was agitated at ambient temperature for 21 hrs to give an equilibrated mixture of 6'-SL, LNnT, LST c and lactose with ca. 38% conversion. The obtained solution was subjected to diafiltration (DF) in the cross-flow MMS SW18 filtration system with installed Trisep UA60 membrane (piperazine PA, MWCO 1000-3500 Da, measured MgSO$_4$ rejection is 89%, spiral-wound, size 1812, area 0.23 m$^2$) at p=15-20 bar and T=25-30° C. with DF water (flow rate in the range of 3-4.5 l/h, matching approximately the permeate flow rate). During the process, additional amount of enzyme was added periodically by small portions (7×50 mg, 300 mg in total). pH was measured periodically and adjusted if necessary by adding small amount of sodium acetate to keep it in the range of 4.5-5.5. After consumption of 25 l of water, the permeate collection was paused overnight while keeping the reaction mixture circulating slowly in the system at low temperature (+8° C.). Next day DF continued with another 25 l of water under the same conditions. The obtained retentate was pumped out from the system (746 g) and the remaining dead volume was removed by washing with two portions of water (2×350 ml). The obtained diluted retentate (1448 g) was heated up to 85° C. in 30 min. The obtained suspension was allowed to cool, treated with charcoal, filtered and the filtrate was concentrated and freeze-dried to give 83.54 g of a colourless solid. Analytical samples were periodically taken and analysed by HPLC. The obtained amounts and conversion are summarized in the table below.

| | Volume/mass | 6'-SL | lactose | LST c | LNnT | conversion |
|---|---|---|---|---|---|---|
| Initial | 950 ml | 80 g | — | — | 60 g | |
| MW (Da) | | 655.5 (Na-salt) | 342 | 997 | 707 | |
| t = 2 min (mmol) | 1000 ml | 125 | — | — | 82.38 | |
| t = 21 h (before DF, mmol) | 1000 ml | 97.8 | 31.1 | 31.1 | 51.26 | 37.9% |
| permeate 1, 0-25l (mmol) | 251 | 1.78 | 41.41 | 2.63 | 4.44 | |
| permeate 2, 25-50l (mmol) | 251 | 0.89 | 9.82 | 1.72 | 1.94 | |
| combined permeate (mmol) | 501 | 2.68 | 51.23 | 4.35 | 6.38 | |
| final diluted retentate after DF with 50l water (mmol) | 1448 g | 34.46 | 0 | 46.57 | 10.30 | |
| permeate + retentate (mmol) | | 37.14 | 51.23 | 50.92 | 16.68 | 75.4% |

Example 3

Flat sheet membranes (d=20 cm, active membrane area 280 cm² for each sheet) were installed into a cross-flow flat sheet cell of the MMS SW18 membrane filtration system. Pure water was equilibrated at 10 bars and 23-25° C. with constant cross-flow (300 l/h) for at least 10 min. Then small portion (5-30 ml) of permeate fractions were collected and exact mass or volume was measured. Flux was calculated according to the following formula: F=V/(t·A) where V is the collected permeate volume in litres, t is the time required to collect the measured volume in hours and A is the membrane area in m².

The following pure water flux values were measured:

| membrane | active layer | MWCO | flux (l/m²h) |
|---|---|---|---|
| Trisep UA60 | piperazine-PA | 1000-3500 | 100.8 |
| GE GH | PA | 2500 | 17 |
| NTR-7450 | sulph. PES | 600-800 | 99.6 |

Then, for the Trisep UA60 and Nitto-Denko NTR-7450 membranes, water was replaced by a feed solution which was prepared as follows: crude LNnT solid sample was obtained from fermentation broth after cell removal by UF (15 kDa), NF (150-300 Da) with diafiltration, decolouration with activated charcoal and freeze-drying. The obtained solid contained LNnT (54.6%), lactose (9.86%), lacto-N-triose II (7.32%) and pLNnH (8.67%, all by weight), from which 41 g was dissolved in 2050 g of water, obtaining a solution having a pH of 5.71 and conductivity of 0.825 mS/cm. The flux of the feed solution was measured under the same conditions.

Then the membranes were washed with pure water (cleaning in place, CIP1), and water flux was re-measured.

Following this, the membranes were washed with an aqueous cleaning solution containing 0.1% sodium dodecyl sulphate, 0.5% EDTA and 0.5% sodium tripolyphosphate (cleaning in place, CIP2, 30 min, 5 bar, 20-25° C.), and water flux was remeasured.

The data show that the NTR-7450 membrane is more prone to being fouled than Trisep UA60 when a pre-treated oligosaccharide solution obtained after fermentation is applied. Furthermore, while pure water washing regenerated the Trisep UA60 membrane to reach 85% of the original water flux, it was inefficient to do so for the NTR-7450 membrane. In addition, whereas a detergent containing cleaning solution completely cleaned the Trisep UA60 membrane, the NTR-4750 membrane was regenerated only partially.

| | flux (l/m²h) | |
|---|---|---|
| | Trisep UA60 | NTR-7450 |
| initial water flux | 100.8 | 99.6 |
| flux with feed solution | 55.1 | 30.3 |
| water flux after CIP1 | 85.4 | 23.9 |
| after CIP1 relative to initial | 85% | 24% |
| water flux after CIP2 | 119 | 71.3 |
| after CIP2 relative to initial | 118% | 72% |

The invention claimed is:

1. A method for producing a compound Gly-A, comprising the steps of:
   a) initiating an enzymatic reaction of compound A and glycosylated compound B (Gly-B) in the presence of a glycosidase capable of transferring the glycosyl (Gly) moiety to compound A;
   b) allowing the reaction in step a) to reach equilibrium to form a first mixture comprising compound A, Gly-B, glycosylated compound A (Gly-A), and compound B;
   c) contacting the mixture with a nanofiltration membrane with a molecular weight cut-off (MWCO) of 600-3500 Da allowing at least a part of compound B to pass and ensuring the retention of compounds Gly-A, compound A and Gly-B, wherein the active (top) layer of the membrane is composed of polyamide, and wherein the MgSO4 rejection of the membrane is 50-90%;
   d) re-initiating an enzymatic reaction of compound A and Gly-B of the retentate the presence of Gly-A and a glycosidase capable of transferring the glycosyl (Gly) moiety to compound A to form a second mixture;
   e) collecting the Gly-A from the second mixture;
   wherein compound A is a tri- or higher oligosaccharide, Gly-A is compound A glycosylated with the Gly moiety, compound B is a disaccharide, and GlyB is compound B glycosylated with the Gly moiety, provided that compounds A and Gly-B are not identical.

2. The method according to claim 1, wherein the MgSO4 rejection of the membrane is 80-90%.

3. The method according to claim 1, wherein the NaCl rejection of the membrane is lower than the MgSO4 rejection.

4. The method according to claim 3, wherein the NaCl rejection of the membrane is not more than 30%.

5. The method according to claim 1, wherein the method comprises diafiltration.

6. The method according to claim 1, wherein the polyamide nanofiltration membrane is a thin-film composite (TFC) membrane.

7. The method according to claim 1, wherein the pure water flux of the membrane is at least 50 l/m2h.

8. The method according to claim 1, wherein the polyamide nanofiltration membrane is a piperazine/based polyamide membrane.

9. The method according to claim 1, wherein the disaccharide is lactose.

10. The method according to claim 1, wherein the glycosyl moiety is fucosyl and the glycosidase is a fucosidase or a transfucosidase, or the glycosyl moiety is sialyl and the glycosidase is a sialidase or a transsialidase.

11. The method according to claim 1, wherein
   Gly-B is 3-O-fucosyllactose (3-FL), A is lacto-N-tetraose (LNT), Gly-A is lacto-N-fucopentaose II (LNFP-II), and the glycosidase is an α1,3/4-(trans)fucosidase,
   Gly-B is 3-O-fucosyllactose (3-FL), A is lacto-N-neotetraose (LNnT), Gly-A is lacto-N-fucopentaose III (LNFP-III), and the glycosidase is an α1,3/4-(trans)fucosidase,
   Gly-B is 3-O-fucosyllactose (3-FL), A is lacto-N-fucopentaose I (LNFP-I), Gly-A is lacto-N-difucohexaose I (LNDFH-I), and the glycosidase is an α1,3/4-(trans)fucosidase,
   Gly-B is 3-O-fucosyllactose (3-FL), A is 2'-O-fucosyllactose (2'-FL), Gly-A is difucosyllactose (DFL), and the glycosidase is an α1,3/4-(trans)fucosidase,
   Gly-B is 2'-O-fucosyllactose (2'-FL), A is 3-O-fucosyllactose (3-FL), Gly-A is difucosyllactose (DFL), and the glycosidase is an α1,2-(trans)fucosidase, Gly-B is 3'-O-sialyllactose (3'-SL), A is 3-O-fucosyllactose (3-FL), Gly-A is 3-O-fucosyl-3'-O-sialyllactose (FSL), and the glycosidase is an α2,3-transsialidase, Gly-B is 3-O-fucosyllactose (3-FL), A is 3'-O-sialyllactose (3'-SL), Gly-A is 3-O-fucosyl-3'-O-sialyllactose (FSL), and the glycosidase is an α1,3/4-(trans)fucosidase, Gly-B is 3'-O-sialyllactose (3'-SL), A is lacto-N-tetraose (LNT), Gly-A is LST a, and the glycosidase is an α2,3-transsialidase, Gly-B is 6'-O-sialyllactose (6'-SL), A is lacto-N-neotetraose (LNnT), Gly-A is LST c, and the glycosidase is an α2,6-(trans)sialidase, Gly-B is 3-O-fucosyllactose (3-FL), A is para-lacto-N-neohexaose (pLNnH), Gly-A is a fucosylated pLNnH, and the glycosidase is an α1,3/4-(trans)fucosidase, or Gly-B is 6'-O-sialyllactose (6'-SL), A is para-lacto-N-neohexaose (pLNnH), Gly-A is a sialylated pLNnH, and the glycosidase is an α2,6-(trans)sialidase.

12. A method for improving conversion of product formation of compound Gly-A comprising the steps of:
a) initiating an enzymatic reaction of compound A and glycosylated compound B (Gly-B) in the presence of a glycosidase capable of transferring the glycosyl (Gly) moiety to compound A;
b) allowing the reaction in step a) to reach equilibrium to form a first mixture comprising compound A, Gly-B, glycosylated compound A (Gly-A), and compound B;
c) contacting the mixture with a nanofiltration membrane with a molecular weight cut-off (MWCO) of 600-3500 Da allowing at least a part of compound B to pass and ensuring the retention of compounds Gly-A, compound A and Gly-B, wherein the active (top) layer of the membrane is composed of polyamide, and wherein the MgSO4 rejection of the membrane is 50-90%;
d) re-initiating an enzymatic reaction of compound A and Gly-B of the retentate the presence of Gly-A and a glycosidase capable of transferring the glycosyl (Gly) moiety to compound A to form a second mixture;
e) collecting the Gly-A from the second mixture;
wherein compound A is a tri- or higher oligosaccharide, Gly-A is compound A glycosylated with the Gly moiety, compound B is a disaccharide, and GlyB is compound B glycosylated with the Gly moiety, provided that compounds A and Gly-B are not identical.

13. The method according to claim 12, wherein the MgSO4 rejection of the membrane is 80-90%.

14. The method according to claim 12, wherein the NaCl rejection of the membrane is lower than the MgSO4 rejection.

15. The method according to claim 14, wherein the NaCl rejection of the membrane is not more than 30%.

16. The method according to claim 12, wherein the method comprises diafiltration.

17. The method according to claim 12, wherein the polyamide nanofiltration membrane is a thin-film composite (TFC) membrane.

18. The method according to claim 12, wherein the polyamide nanofiltration membrane is a piperazine/based polyamide membrane.

19. The method according to claim 12, wherein the disaccharide is lactose.

20. The method according to claim 12, wherein
Gly-B is 3-O-fucosyllactose (3-FL), A is lacto-N-tetraose (LNT), Gly-A is lacto-N-fucopentaose II (LNFP-II), and the glycosidase is an α1,3/4-(trans)fucosidase, Gly-B is 3-O-fucosyllactose (3-FL), A is lacto-N-neotetraose (LNnT), Gly-A is lacto-N-fucopentaose III (LNFP-III), and the glycosidase is an α1,3/4-(trans)fucosidase, Gly-B is 3-O-fucosyllactose (3-FL), A is lacto-N-fucopentaose I (LNFP-I), Gly-A is lacto-N-difucohexaose I (LNDFH-I), and the glycosidase is an α1,3/4-(trans)fucosidase, Gly-B is 3-O-fucosyllactose (3-FL), A is 2'-O-fucosyllactose (2'-FL), Gly-A is difucosyllactose (DFL), and the glycosidase is an α1,3/4-(trans)fucosidase, Gly-B is 2'-O-fucosyllactose (2'-FL), A is 3-O-fucosyllactose (3-FL), Gly-A is difucosyllactose (DFL), and the glycosidase is an α1,2-(trans)fucosidase, Gly-B is 3'-O-sialyllactose (3'-SL), A is 3-O-fucosyllactose (3-FL), Gly-A is 3-O-fucosyl-3'-O-sialyllactose (FSL), and the glycosidase is an α2,3-transsialidase, Gly-B is 3-O-fucosyllactose (3-FL), A is 3'-O-sialyllactose (3'-SL), Gly-A is 3-O-fucosyl-3'-O-sialyllactose (FSL), and the glycosidase is an α1,3/4-(trans)fucosidase, Gly-B is 3'-O-sialyllactose (3'-SL), A is lacto-N-tetraose (LNT), Gly-A is LST a, and the glycosidase is an α2,3-transsialidase, Gly-B is 6'-O-sialyllactose (6'-SL), A is lacto-N-neotetraose (LNnT), Gly-A is LST c, and the glycosidase is an α2,6-(trans)sialidase, Gly-B is 3-O-fucosyllactose (3-FL), A is para-lacto-N-neohexaose (pLNnH), Gly-A is a fucosylated pLNnH, and the glycosidase is an α1,3/4-(trans)fucosidase, or Gly-B is 6'-O-sialyllactose (6'-SL), A is para-lacto-N-neohexaose (pLNnH), Gly-A is a sialylated pLNnH, and the glycosidase is an α2,6-(trans)sialidase.

* * * * *